(12) United States Patent
Tanner et al.

(10) Patent No.: US 11,512,342 B1
(45) Date of Patent: Nov. 29, 2022

(54) COMPOSITIONS AND METHODS FOR DETECTING PYROPHOSPHATE PRODUCTS OF ENZYME REACTIONS USING PYRIDYLAZOANILINE DYES

(71) Applicant: New England Biolabs, Inc., Ipswich, MA (US)

(72) Inventors: Nathan Tanner, West Newbury, MA (US); Ivan R. Correa, Jr., Hamilton, MA (US); Yinhua Zhang, North Reading, MA (US); Ece Alpaslan, Malden, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 17/661,954

(22) Filed: May 4, 2022

Related U.S. Application Data

(60) Provisional application No. 63/263,361, filed on Nov. 1, 2021, provisional application No. 63/263,364, filed on Nov. 1, 2021.

(51) Int. Cl.
| | | |
|---|---|---|
| *C12Q 1/68* | (2018.01) | |
| *C12Q 1/6816* | (2018.01) | |
| *C12Q 1/6844* | (2018.01) | |
| *C12Q 1/6876* | (2018.01) | |

(52) U.S. Cl.
CPC ......... *C12Q 1/6816* (2013.01); *C12Q 1/6846* (2013.01); *C12Q 1/6876* (2013.01)

(58) Field of Classification Search
CPC .. C12Q 1/6816; C12Q 1/6846; C12Q 1/6876; C09B 29/0003
See application file for complete search history.

(56) References Cited

U.S. PATENT DOCUMENTS

| | | | |
|---|---|---|---|
| 8,993,298 | B1 | 3/2015 | Ong et al. |
| 9,034,606 | B2 | 5/2015 | Tanner et al. |
| 9,127,258 | B2 | 9/2015 | Ong et al. |
| 9,157,073 | B1 | 10/2015 | Ong et al. |
| 9,447,445 | B2 | 9/2016 | Hsieh et al. |
| 9,580,748 | B2 | 2/2017 | Tanner et al. |
| 9,963,687 | B2 | 5/2018 | Hsieh et al. |
| 10,253,357 | B2 | 4/2019 | Mitra et al. |
| 11,162,133 | B2 | 11/2021 | Zhang et al. |
| 2011/0117549 | A1 | 5/2011 | Miyamoto et al. |

FOREIGN PATENT DOCUMENTS

| | | | |
|---|---|---|---|
| EP | 2751264 A1 | | 7/2014 |
| WO | WO-2022101259 A1 | * | 5/2022 |

OTHER PUBLICATIONS

Notomi, et al. Loop-mediated isothermal amplification of DNA. Nucleic Acids Res 28(12), E63 (2000).
Tanner, et al. Simultaneous multiple target detection in real-time loop-mediated isothermal amplification. Biotechniques 53(2), 81-89 (2012).
Ball, et al. Quenching of Unincorporated Amplification Signal Reporters in Reverse-Transcription Loop-Mediated Isothermal Amplification Enabling Bright, Single-Step, Closed-Tube, and Multiplexed Detection of RNA Viruses. Anal Chem 88(7), 3562-3568 (2016).
Liu, et al. Establishment of an accurate and fast detection method using molecular beacons in loop-mediated isothermal amplification assay. Sci Rep 7 40125 (2017).
Bakthavathsalam, et al. Locked nucleic acid molecular beacon for multiplex detection of loop mediated isothermal amplification. Sensors and Actuators B: Chemical 268 255-263 (2018).
Little, et al. Strand displacement amplification and homogeneous real-time detection incorporated in a second-generation DNA probe system, BDProbeTecET. Clin Chem 45(6 Pt 1), 777-784 (1999).
Nadeau, et al. Real-time, sequence-specific detection of nucleic acids during strand displacement amplification. Anal Biochem 276(2), 177-187 (1999).
Piepenburg, et al. DNA detection using recombination proteins. PLoS Biol 4(7), e204 (2006).
Deiman, et al. Characteristics and applications of nucleic acid sequence-based amplification (NASBA). Mol Biotechnol 20(2), 163-179 (2002).
Jothikumar, et al. Visual endpoint detection of *Escherichia coli* O157:H7 using isothermal Genome Exponential Amplification Reaction (GEAR) assay and malachite green. J Microbiol Methods 98 122-127 (2014).
Nzelu, et al. Development of a loop-mediated isothermal amplification method for rapid mass-screening of sand flies for Leishmania infection. Acta Trap 132 1-6 (2014).
Miori, et al. Detection of loop-mediated isothermal amplification reaction by turbidity derived from magnesium gyrophosphate formation. Biochem Biophys Res Commun 289(1), 150-154 (2001).
Soto, et al. Colorimetric detection of loop-mediated isothermal amplification reaction by using hydroxy naphthol blue. Biotechniques 46(3), 167-172 (2009).

(Continued)

*Primary Examiner* — Jezia Riley
(74) *Attorney, Agent, or Firm* — New England Biolabs, Inc; Harriet M. Strimpel

(57) ABSTRACT

Provided herein is a composition comprising an enzyme that releases pyrophosphate from a substrate and a dye of Formula 1. A method for detecting pyrophosphate is also provided. A kit comprising a polymerase that releases pyrophosphate by hydrolysis of nucleoside triphosphates during nucleic acid replication, a divalent manganese salt, and the dye are also provided. The present composition, method and kits provide a way to detect and/or quantify substrates or products of enzyme reacted substrates associated with the release pyrophosphate (e.g., nucleic acid amplification reactions and other reactions that hydrolyze ATP) via a distinct color change without substantially affecting the sensitivity and/or specificity of the reaction.

29 Claims, 23 Drawing Sheets
(12 of 23 Drawing Sheet(s) Filed in Color)
Specification includes a Sequence Listing.

(56) References Cited

OTHER PUBLICATIONS

Wang, Visual Detection of *Mycobacterium tuberculosis* Complex with Loop-Mediated Isothermal Amplification and Eriochrome Black T. Applied Mechanics and Materials 618 264-267 (2014).
Nguyen, et al. Quantification of colorimetric isothermal amplification on the smartphone and its open-source app for point-of-care pathogen detection. Scientific Reports 10(1), 15123 (2020).
Tomita, et al. Loop-mediated isothermal amplification (LAMP) of gene sequences and simple visual detection of products. Nat Protoc 3(5), 877-882 (2008).
Tanner, et al. Visual detection of isothermal nucleic acid amplification using pH-sensitive dyes. Biotechniques 58(2), 59-68 (2015).
Calvert, et al. Rapid colorimetric detection of Zika virus from serum and urine specimens by reverse transcription loop-mediated isothermal amplification (RT-LAMP). PLoS One 12(9), e0185340 (2017).
Vo, et al. Facile and direct detection of human papillomavirus (HPV) DNA in cells using loop-mediated isothermal amplification (LAMP). Mol Cell Probes 59 101760 (2021).
Goncalves, et al. Detecting wMel Wolbachia in field-collected *Aedes aegypti* mosquitoes using loop-mediated isothermal amplification (LAMP). Parasit Vectors 12(1), 404 (2019).
Romero, et al. A rapid, sensitive and inexpensive method for detection of grapevine red blotch virus without tissue extraction using loop-mediated isothermal amplification Arch Virol 164(5), 1453-1457 (2019).
Choudhary, et al. LAMP assay for detection of Rhizoctonia solani AG-1 IA causing sheath blight of rice. Sci Rep 10 (1), 22022 (2020).
Rafiq, et al. Development of a LAMP assay using a portable device for the real-time detection of cotton leaf curl disease in field conditions. Biol Methods Protoc 6(1), bpab010 (2021).
Anathar, et al. Clinical Assessment and Validation of a Rapid and Sensitive SARS-CoV-2 Test Using Reverse Transcription Loop-Mediated Isothermal Amplification Without the Need for RNA Extraction. Open Forum Infectious Diseases 8(2), (2020).
Dao, et al. A colorimetric RT-LAMP assay and LAMP-sequencing for detecting SARS-CoV-2 RNA in clinical samples. Science Translational Medicine 12(556), eabc7075 (2020).
Emergency Use Authorization (EUA) Summary for the Color SARS-COV-2 RT-Lamp Diagnostic Assay (https://www.fda.gov/media/138249/download), 2021.
Lamb, et al. Rapid detection of novel coronavirus/Severe Acute Respiratory Syndrome Coronavirus 2 (SARS-CoV-2) by reverse transcription-loop-mediated isothermal amplification. PLoS One 15(6), e0234682 (2020).
Rabe, et al. SARS-CoV-2 detection using isothermal amplification and a rapid, inexpensive protocol for sample inactivation and purification. Proc Natl Acad Sci U S A 117(39), 24450-24458 (2020).
Zhang, et al. Rapid Molecular Detection of SARS-CoV-2 (COVID-19) Virus RNA Using Colorimetric LAMP https://www.medrxiv.org/content/10.1101/2020.02.26.20028373v1.full.pdf+html (2020).
Amaral, et al. A molecular test based on RT-LAMP for rapid, sensitive and inexpensive colorimetric detection of SARS-CoV-2 in clinical samples. Sci Rep 11(1), 16430 (2021).
Baba, et al. Diagnostic performance of a colorimetric RT-LAMP for the identification of SARS-CoV-2: A multicenter prospective clinical evaluation in sub-Saharan Africa EClinicalMedicine 40 101101 (2021).
Lalli, et al. Rapid and Extraction-Free Detection of SARS-CoV-2 from Saliva by Colorimetric Reverse-Transcription Loop-Mediated Isothermal Amplification. Clinical chemistry 67(2), 415-424 (2021).
Lucira COVID-19 All-In-One Test Kit (https://www.fda.gov/media/143810/download), 2020.
Uribe-Alvarez, et al. Low saliva pH can yield false positives results in simple RT-LAMP-based SARS-CoV-2 diagnostic tests. PLoS One 16(5), e0250202 (2021).
Horiguchi, et al. Water Soluble Pyridylazoaminophenols and Pyridylazoaminobenzoic Acids as Highly Sensitive Photometric Reagents for Zinc, Uranium, Cobalt and Nickel. Analytical Sciences 1(5), 461-465 (1985).
Inoue, et al. Colorimetric Co2+ sensor based on an anionic pyridylazo dye and a cationic polyelectrolyte in aqueous solution. Polymer International 67(12), 1589-1594 (2018).
Fukushima, et al. Colorimetric detection of Mn(ii) based on a mixture of an anionic pyridylazo dye and a cationic polyelectrolyte in aqueous solution. Coloration Technology 136(5), 450-456 (2020).
Fukushima, et al. Colorimetric detection of homocysteine by a pyridylazo dye-based Cu2+ complex via indicator displacement mechanism. Analytical Biochemistry 621 114185 (2021).
Zhang, et al. Enhancing colorimetric loop-mediated isothermal amplification speed and sensitivity with guanidine chloride. Biotechniques 69(3), 178-185 (2020).

* cited by examiner wherein:

R1 and R5 are each independently selected from the group consisting of H, halogen, nitro, cyano, sulfonic acid, carboxy, trifluoromethyl, trichloromethyl and tribromomethyl;

R2 and R3 are each independently a lower alkyl optionally comprising a terminal sulfonate group; and R4 is H, OH or COOH.

5-Bromo-PAPS

5-Nitro-PAPS

3,5-DiBromo-PAESA

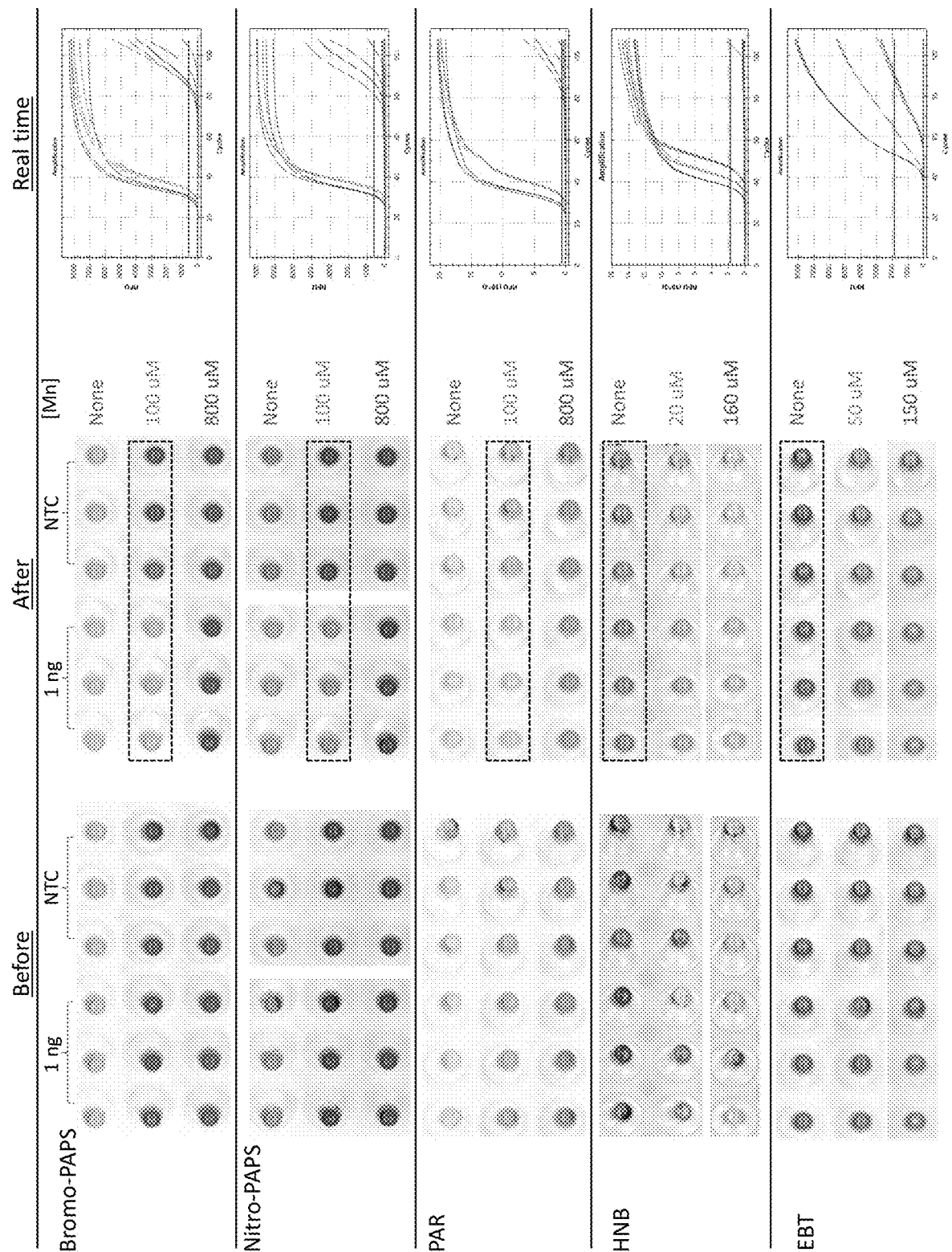

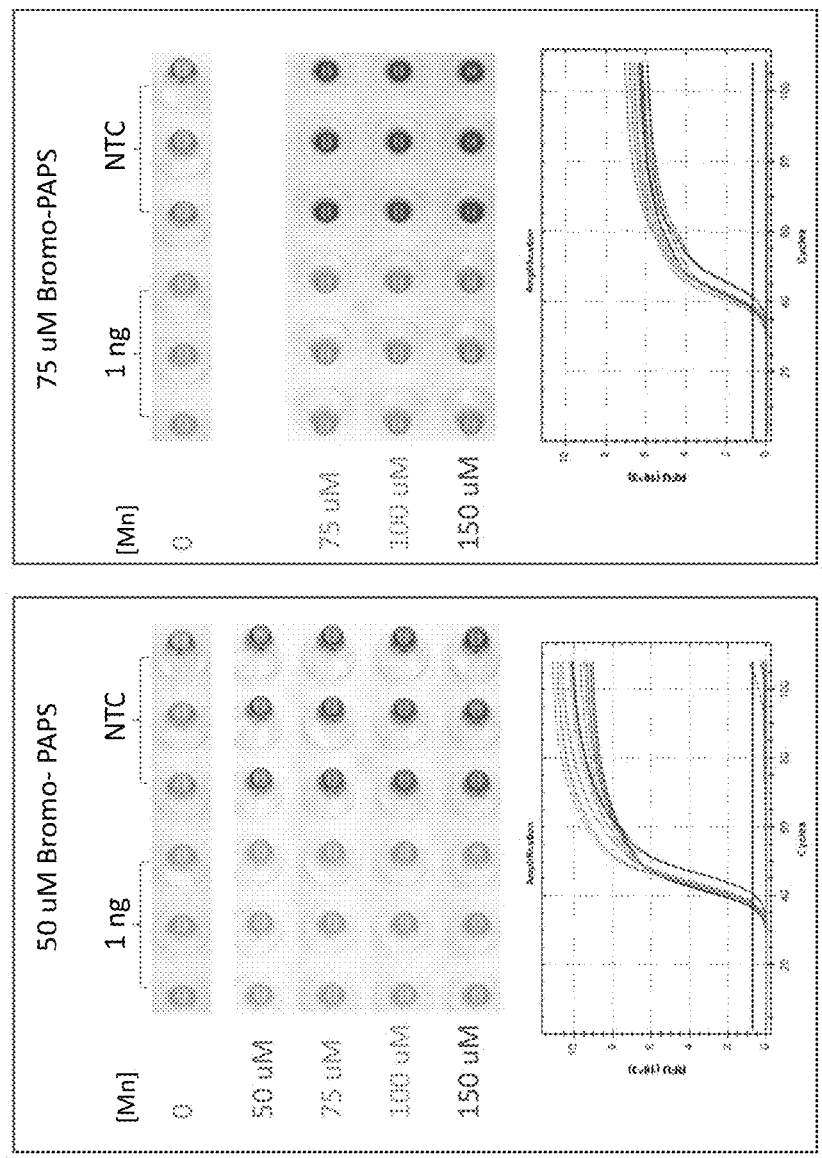
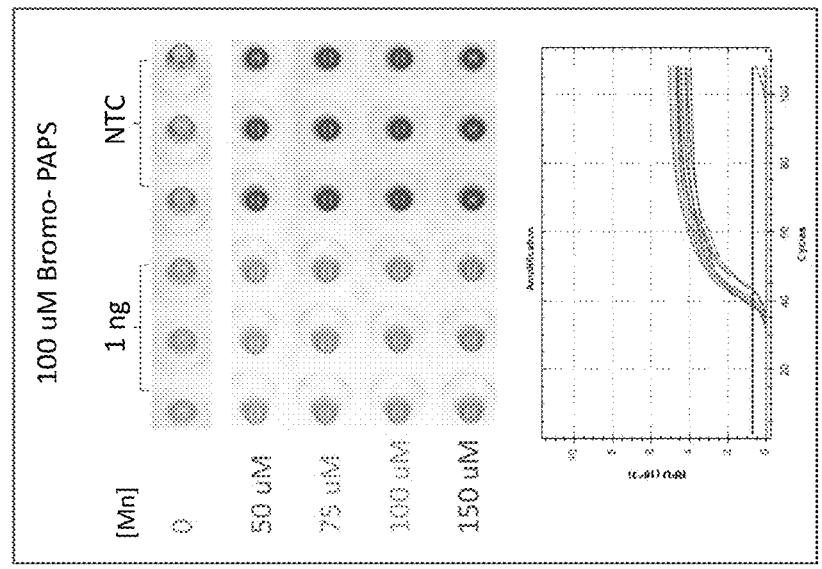
FIG. 4A  FIG. 4B  FIG. 4C

After LAMP

Before LAMP

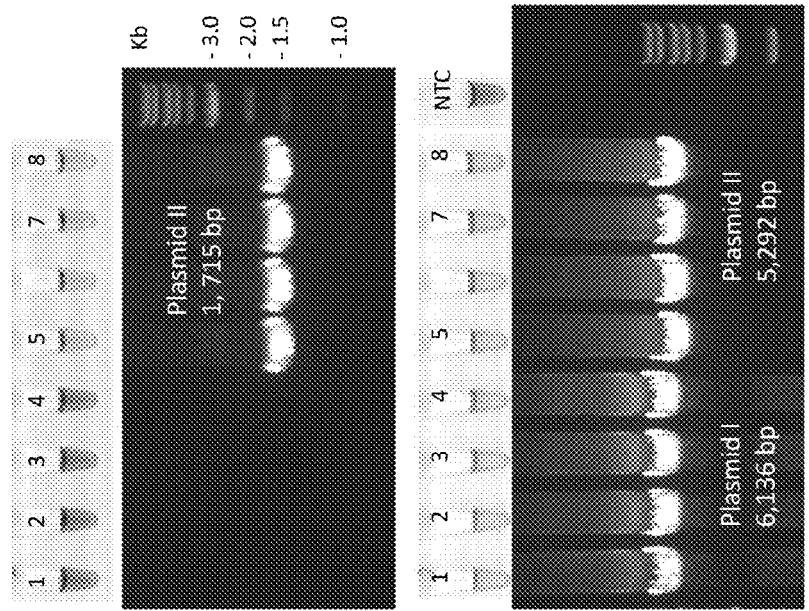
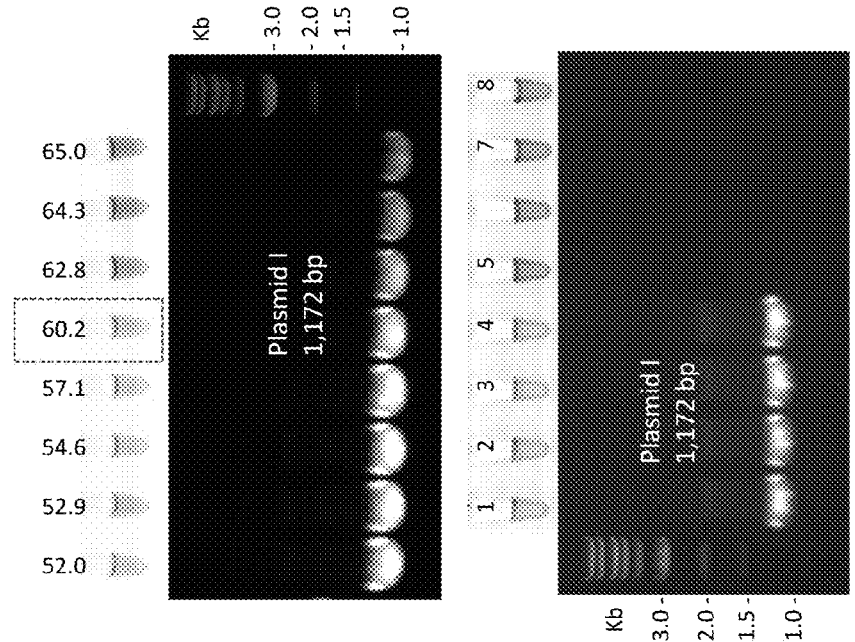
FIG. 9A   FIG. 9B   FIG. 9C   FIG. 9D

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
cctgctctgc cgcttcacgc                                              20

<210> SEQ ID NO 2
<211> LENGTH: 28
<212> TYPE: DNA
<213> ORGANISM: Artificial Sequence
<220> FEATURE:
<223> OTHER INFORMATION: Synthetic construct

<400> SEQUENCE: 2
tccggataaa aacgtcgatg acatttgc                                     28

<210> SEQ ID NO 3
<211> LENGTH: 28
<212> TYPE: DNA
<213> ORGANISM: Artificial Sequence
<220> FEATURE:

<223> OTHER INFORMATION: Synthetic construct

<400> SEQUENCE: 3
gatgacgcat cctcacgata atatccgg                                               28

<210> SEQ ID NO 4
<211> LENGTH: 24
<212> TYPE: DNA
<213> ORGANISM: Artificial Sequence
<220> FEATURE:
<223> OTHER INFORMATION: Synthetic construct

<400> SEQUENCE: 4
ccatgattca gtgtgcccgt ctgg                                                   24

<210> SEQ ID NO 5
<211> LENGTH: 23
<212> TYPE: DNA
<213> ORGANISM: Artificial Sequence
<220> FEATURE:
<223> OTHER INFORMATION: Synthetic construct

<400> SEQUENCE: 5
cgaacgtcgc gcagagaaac agg                                                    23

<210> SEQ ID NO 6
<211> LENGTH: 26
<212> TYPE: DNA
<213> ORGANISM: Artificial Sequence
<220> FEATURE:
<223> OTHER INFORMATION: Synthetic construct

<400> SEQUENCE: 6
cctggatcca gatgcagtaa taccgc                                                 26

<210> SEQ ID NO 7
<211> LENGTH: 22
<212> TYPE: DNA
<213> ORGANISM: Artificial Sequence
<220> FEATURE:
<223> OTHER INFORMATION: Synthetic construct

<400> SEQUENCE: 7
tccgaggatg gtattcgtca tg                                                     22

<210> SEQ ID NO 8
<211> LENGTH: 24
<212> TYPE: DNA
<213> ORGANISM: Artificial Sequence
<220> FEATURE:
<223> OTHER INFORMATION: Synthetic construct

<400> SEQUENCE: 8
ggggcacctt ctccaactca tact                                                   24

<210> SEQ ID NO 9
<211> LENGTH: 24
<212> TYPE: DNA
<213> ORGANISM: Artificial Sequence
<220> FEATURE:
<223> OTHER INFORMATION: Synthetic construct

<400> SEQUENCE: 9
cgagctacca cgcagacatc aacc                                                   24

```
<210> SEQ ID NO 10
<211> LENGTH: 24
<212> TYPE: DNA
<213> ORGANISM: Artificial Sequence
<220> FEATURE:
<223> OTHER INFORMATION: Synthetic construct

<400> SEQUENCE: 10
ggggcacctt ctccaactca tact                                              24

<210> SEQ ID NO 11
<211> LENGTH: 23
<212> TYPE: DNA
<213> ORGANISM: Artificial Sequence
<220> FEATURE:
<223> OTHER INFORMATION: Synthetic construct

<400> SEQUENCE: 11
cctcatttgg ggagggtta tct                                                23

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
gaagagccaa ggacaggtac                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
cctccaaatc aagcctctac                                                   20
```

COMPOSITIONS AND METHODS FOR DETECTING PYROPHOSPHATE PRODUCTS OF ENZYME REACTIONS USING PYRIDYLAZOANILINE DYES

CROSS-REFERENCING

This application claims the benefit of U.S. provisional application Ser. No. 63/263,361, filed on Nov. 1, 2021, and 63/263,364, filed on Nov. 1, 2021, which applications are incorporated by reference herein.

BACKGROUND

A surprising finding in 2012 by Zhang, et al. and Tanner, et al. was that amplification of a target DNA could be detected in a low concentration buffer by a visual color change of a pH sensitive dye (see U.S. Pat. Nos. 9,034,606, 9,580,148 and 11,162,133). The color change caused by a change in pH was the result of release of hydrogen ions ($H^+$) from deoxyribose nucleoside triphosphates (dNTPs) when they were incorporated into DNA during amplification. The selected dyes did not appear to adversely affect the activity of the polymerase required for amplification; the amplification conditions themselves did not adversely affect a change in color; observable color change occurred as a direct result of amplification; the color change of the dye was readily detectable by eye; and the detection means was sensitive enough to detect low amounts of amplified DNA product where the relatively low concentrations of DNA were either due to the concentration of the starting material or to the number of amplification cycles required to reach a detectable end point.

Previous to these findings, color dyes such as calcein or hydroxynaphthol blue (HNB) were added to an amplification reaction but gave color changes that was ambiguous at best. Goto, et al., Biotechniques, 46, 3, 167-172, 2009, described the use of HNB as a colorimetric reagent for alkaline earth metal ions in loop-mediated isothermal amplification (LAMP) reactions. The color of HNB was pH dependent and was magenta at pH 8.6-pH 9.0 and violet at pH 8.4. Alternatively, color change was induced by a change in magnesium ion concentration irrespective of pH. The maximum absorbance peak was observed at 650 nm in the absence of magnesium with the maximum absorbance peak decreasing as the level of magnesium increased. Because of the ambiguity of the HNB color change visualized by eye resulting from amplification, it was necessary to use some other method of detecting the occurrence of LAMP.

Alternatively, color dyes were added after amplification had occurred to detect DNA amplicons. The dyes would bind to DNA either directly or by intercalation so that the more DNA product that was made, the more the intensity of the color from the dye increased. Because the DNA detection assays were relatively insensitive, a carrier such as a gel were included to increase the local concentration of the DNA and hence the color signal. Alternatively or additionally, some additional reagent might be added with the dye that would change the color of the post-amplification mix so that the solution containing amplified nucleic acid could be differentiated from one that did not. Dyes that were described by Miyamoto, et al. in US 2011/0117549 were triphenylmethane dye, thiazine dye, oxazine dye, azine dye, xanthene dye, and phenanthridinium dye exemplified by Crystal Violet, Gentian Violet B, Victoria Blue B, Methyl Violet, Night Blue, Methyl Green, Toluidine Blue O, Azure B, Methylene Blue, Brilliant Cresol Blue, Methyl Orange, Pyronin Y. Ethidium Bromide, and Neutral Red.

Subsequent to 2012, others reported pH dependent colorimetric detection of nucleic acids using a wider range of pH dyes and buffers (see U.S. Pat. No. 10,253,357) repeating and extending the earlier work described in U.S. Pat. Nos. 9,034,606 and 9,580,148. Although visually detectable dyes were mentioned, these references focused on measuring hue where detecting hue relied on the read-out of a spectrophotometer and various statistical manipulations of the data. This reference recited phenol red, bromocresol purple, bromothymol blue, neutral red, naphtholphthalein, cresol red, cresolphthalein, phenolphthalein, methyl red, and thymolphthalein as examples of pH sensitive dyes. Dye mixtures of phenol red and bromothymol blue, and cresol red and bromothymol blue were also described with buffers having buffering capacities within various pH ranges such as pH 6-pH 9 or pH 6.5-pH 8.8.

Although the pH dependent colorimetric amplification assay with phenol red is very effective, it would be desirable to engineer additional improvements. A limitation of the pH dependent colorimetric amplification assay is the limitation on buffer concentration and the required pH range to differentiate positive from negative samples. An unwanted change in the pH might result from the use of dry ice in shipping containers. Certain biofluid compositions such as a subset of saliva samples or certain types of environmental samples might have a less than ideal pH where avoidance or correction of the undesirable pH is limited by the acceptable amount of buffer (e.g. less than 5 mM Tris buffer for phenol red).

Consequently, an alternative dye or dye family that is compatible with polymerases, does not interfere with amplification reactions and provides a strong binary colorimetric signal that translates into a distinct peak for a positive endpoint that is at a different wavelength from a peak at a negative endpoint in the spectrum and is detectable by eye with use in a variety of different amplification reactions not limited to LAMP would be a useful addition to diagnostic test options.

SUMMARY

Provided herein is a composition comprising an enzyme that releases pyrophosphate from a substrate and a dye of Formula 1:

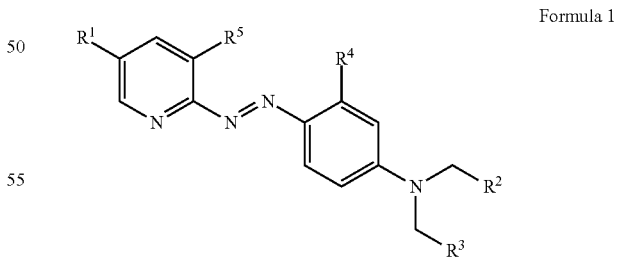

Formula 1 wherein:

R1 and R5 are each independently selected from the group consisting of H, halogen, nitro, cyano, sulfonic acid, carboxy, trifluoromethyl, trichloromethyl and tribromomethyl;

R2 and R3 are each independently a lower alkyl optionally comprising a terminal sulfonate group; and R4 is H, OH or COOH.

In some embodiments, at least one of R1 and R5 is a halogen selected from F, Cl, Br or I, R2 and R3 are each independently n-butyl, sec-butyl, isobutyl, tert-butyl, propyl, n-propyl, isopropyl, ethyl, or methyl; and at least one of R2 and R3 comprises the terminal sulfonate group.

A method for detecting pyrophosphate is also provided. This method may comprise combining a manganese salt, an enzyme (e.g., a polymerase, or another enzyme that hydrolyzes a nucleoside triphosphate (NTP) such as a DNA polymerase, an RNA polymerase, a reverse transcriptase, a primase, a ligase, a helicase, a nucleotide pyrophosphatase (Ppase)/phosphodiesterase, an RNA decapping enzyme (RNA 5' pyrophosphohydrolase) and a geranyl pyrophosphate synthase), a substrate for the enzyme that releases pyrophosphate when it is hydrolyzed (e.g., NTP), and a dye of Formula 1 produce a reaction mix, incubating the reaction mix under conditions by which the enzyme cleaves the substrate to produce pyrophosphate, and observing a change in color of the reaction mix, wherein the change in color indicates that pyrophosphate has been produced.

In some embodiments, the reaction mix may comprise a polymerase, rNTPs or dNTPs, the manganese salt, a template nucleic acid and the dye, the reaction mix is incubated under conditions suitable for amplification of the nucleic acid, and the change in color indicates that a product has been amplified. Amplification methods may include any of loop-mediated isothermal amplification (LAMP), polymerase chain reaction (PCR), strand displacement amplification (SDA), helicase dependent amplification (HDA), multiple displacement amplification (MDA), rolling circle amplification, ligation mediated amplification, whole genome amplification (WGA), nucleic acid sequence-based amplification (NASBA) or recombinase polymerase amplification (RPA) mix.

A kit comprising a polymerase, manganese salt, and the dye are also provided.

The present composition, method and kits are believed to be a significant advancement in the art because they provide a way to measure the progress of reactions that release pyrophosphate (e.g., nucleic acid amplification reactions and other reactions that hydrolyze ATP) via a color change. The dyes used in the present disclosure are one color (e.g., red) when they are bound to a divalent metal cation and another color (e.g., yellow) when they are not bound to the divalent metal cation. Without wishing to be held to any particular theory, it is believed that during these reactions, the liberated pyrophosphate competes with the dye for binding to the metal ion. This competition results in the release of a metal ion from the dye, which is sequestered by the pyrophosphate. Release of the metal ion from the dye restores the dye's original color. In one embodiment, the reaction changes from red to yellow during the course of the reaction, as the pyrophosphate is being produced. The color change can be readily detected by spectrophotometry, image analysis or by eye. By selecting the appropriate detection method, hue or change in peak wavelength can be measured. Embodiments of Formula 1 include 2-(5-Bromo-2-pyridylazo)-5-(N-propyl-N-sulfopropylamino)phenol (5-Br-PAPS), 2-(5-Nitro-2-pyridylazo)-5-(N-propyl-N-sulfopropylamino)phenol (5-Nitro-PAPS) or 3,5-Dibromo-PAESA.

BRIEF DESCRIPTION OF THE FIGURES

The patent or application file contains at least one drawing executed in color. Copies of this patent or patent application publication with color drawings will be provided by the office upon request and payment of the necessary fee.

The skilled artisan will understand that the drawings, described below, are for illustration purposes only. The drawings are not intended to limit the scope of the present teachings in any way.

FIG. 1A shows the structure of a 4-(2-pyridylazo)aniline dye, where:

R1 and R5 are each independently selected from the group consisting of H, halogen, nitro, cyano, sulfonic acid, carboxy, trifluoromethyl, trichloromethyl and tribromomethyl; and R2 and R3 are each independently a lower alkyl optionally comprising a terminal sulfonate group; and R4 is H, OH or COOH.

In some embodiments, at least one of R1 and R5 is a halogen selected from F, Cl, Br or I, and R2 and R3 are each independently n-butyl, sec-butyl, isobutyl, tert-butyl, propyl, n-propyl, isopropyl, ethyl, or methyl and at least one of R2 and R3 comprises the terminal sulfonate group.

FIGS. 1C-1G show two 4-(2-pyridylazo)aniline metal sensing dyes, 5-Bromo-PAPS and 5-Nitro-PAPS (2-(2-pyridylazo)-5-(N-propyl-N-sulfopropylamino) phenol that performed significantly better than other non-aniline azo metal sensing dyes 4-(2-pyridylazo)resorcinol) (PAR), hydroxynaphthol blue (HNB) and eriochrome black T (EBT) as indicators of a positive LAMP reaction under the same conditions.

Left plate of 18 wells (before LAMP) and right plate of 18 wells (after LAMP) show the color of triplicate LAMP reactions with either lambda DNA (1 ng) or without (NTC). Each dye was tested using 0 µM $Mn^{2+}$, 100 µM $Mn^{2+}$ and 800 µM $Mn^{2+}$. The labels for these three conditions are color-coded the same as their corresponding real-time curves on the right side of the figure that confirm that LAMP occurred. The best visual detection condition for each dye after LAMP is highlighted in the right plate with a dotted rectangle around 6 samples.

FIG. 1C shows the results with 75 µM 5-Bromo-PAPS.
FIG. 1D shows the results with 75 µM 5-Nitro-PAPS.
FIG. 1E shows the results with 200 µM PAR.
FIG. 1F shows the results with 80 µM HNB.
FIG. 1G shows the results with 100 µM EBT.

FIG. 2A-2D showed that of the 9 different metal salts tested, manganese ions gave the clearest color change for 5-Bromo-PAPS and 5-Nitro-PAPS.

Figures 2A, 2B:
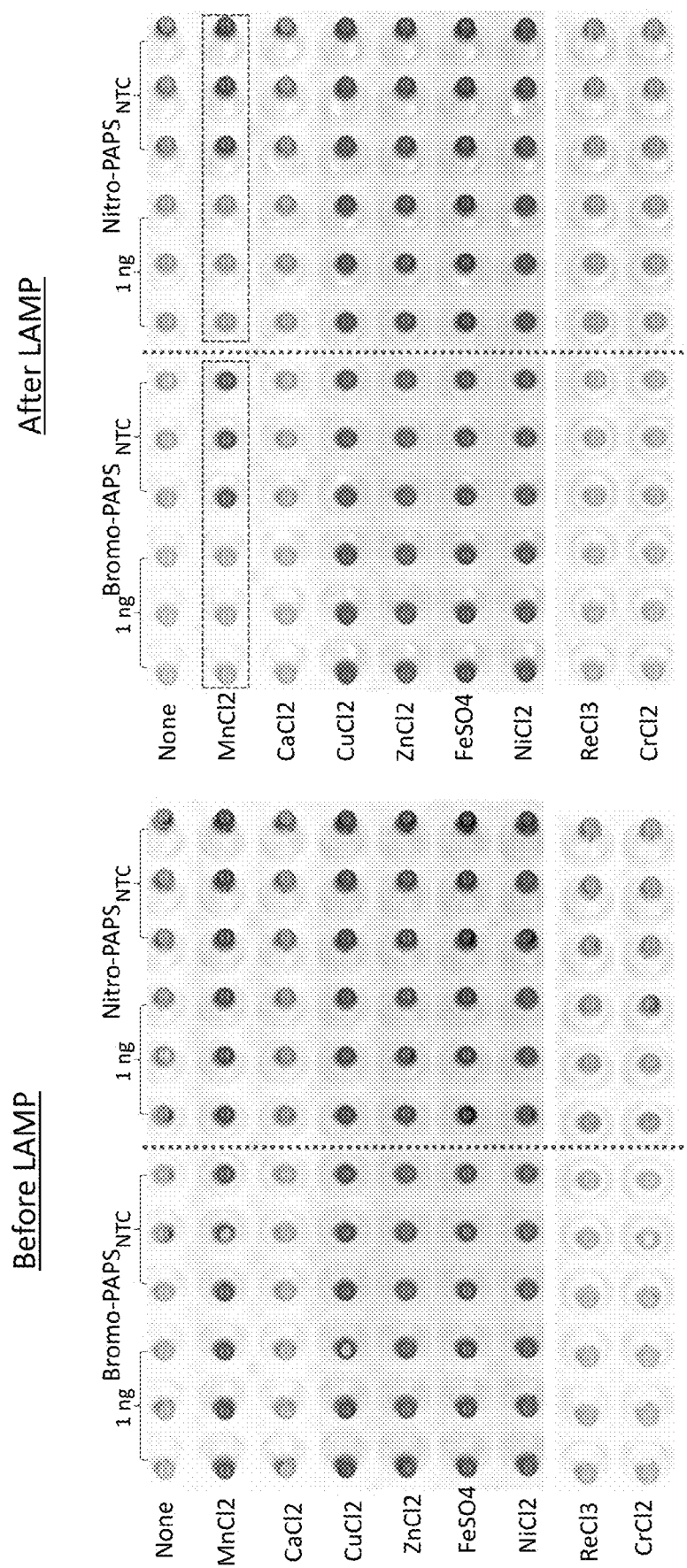

In FIG. 2A (before LAMP) and FIG. 2B (after LAMP), $Mn^{2+}$ gave an optimal signal of yellow to red with PAPS dyes in response to LAMP amplification using 100 µM metal ion with 75 µM 5-Bromo-PAPS or 5-Nitro-PAPS in triplicates with or without 1 ng Lambda DNA (1 ng).

Figure 2C:
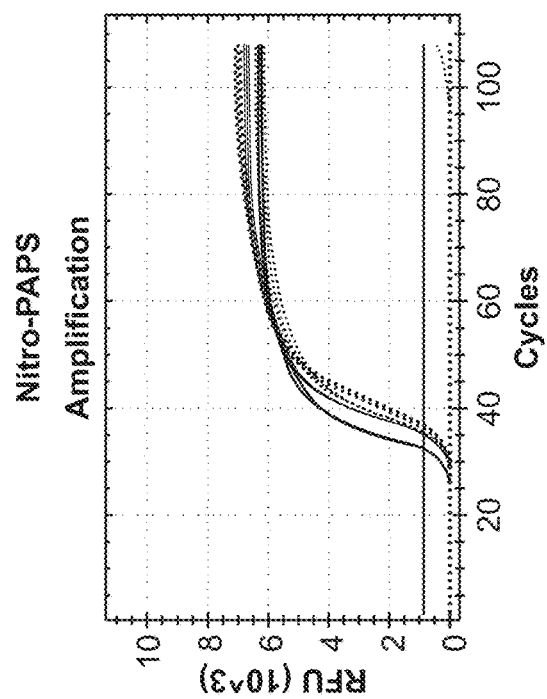
Figure 2C:
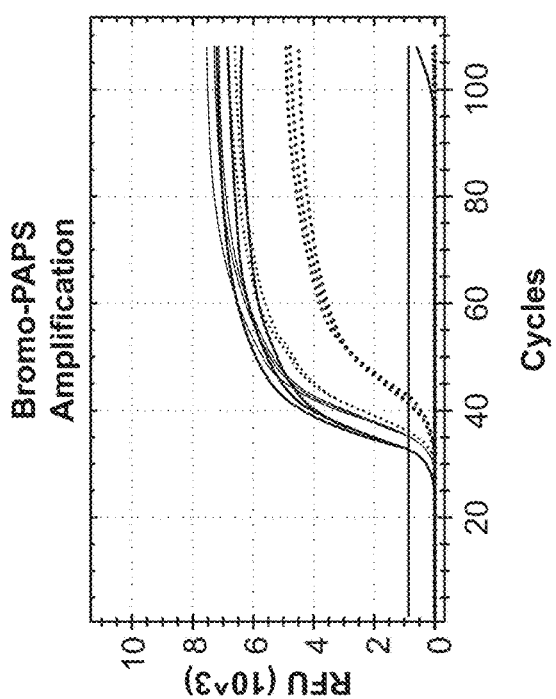
Figure 2D:
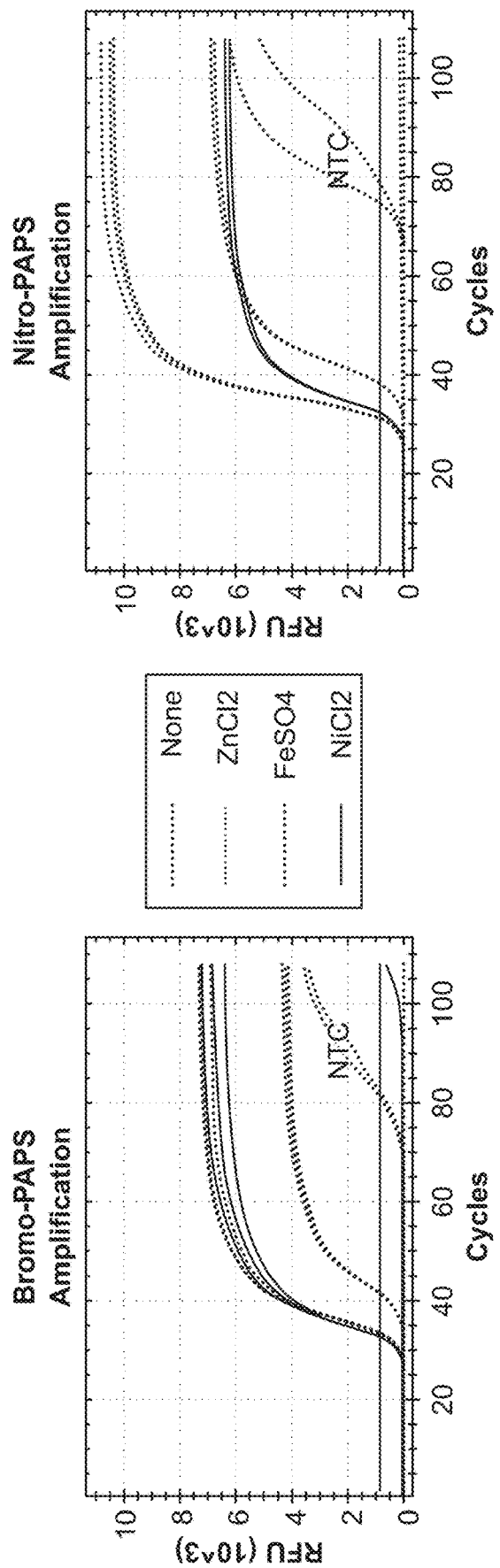

FIG. 2C and FIG. 2D show corresponding real time curves for samples in FIG. 2A and FIG. 2B. The reactions with $Mn^{2+}$ are highlighted with dashed rectangles.

Figure 3A:
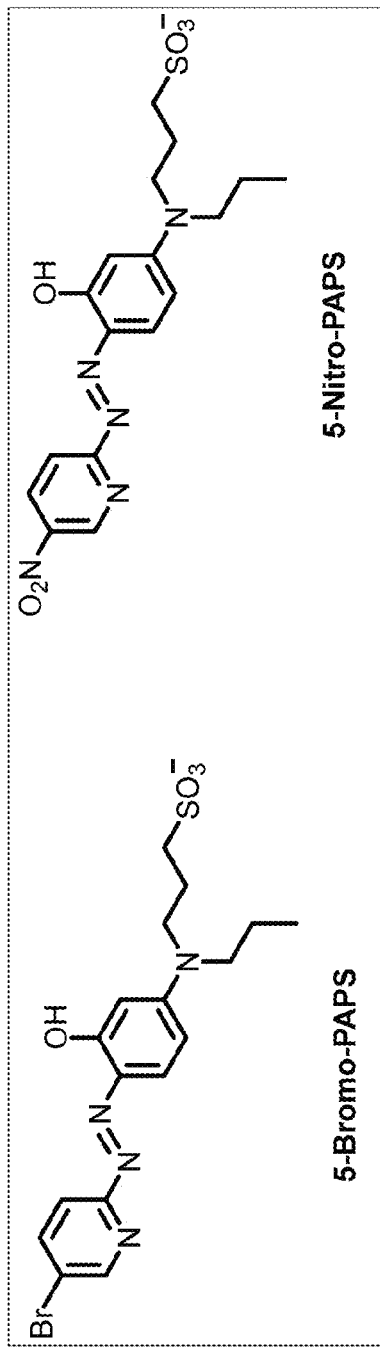
Figure 3B:
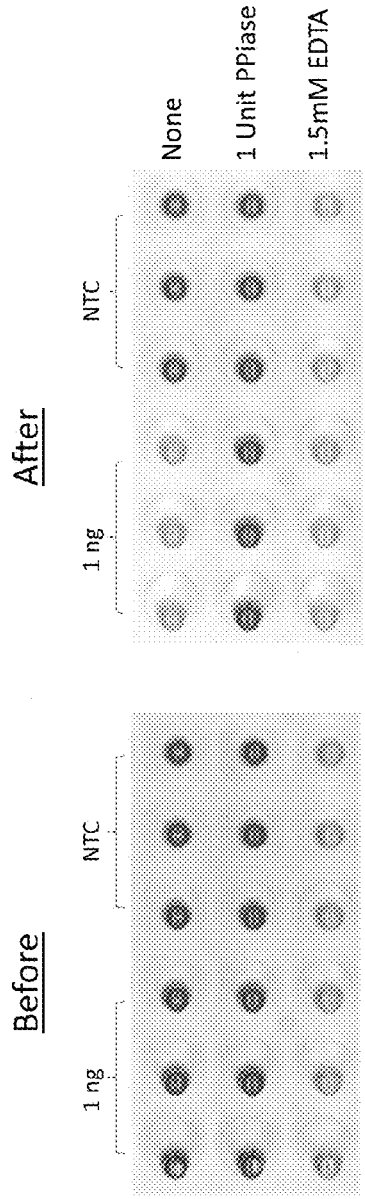
Figure 3C:

FIGS. 3A-3C show that pyrophosphates released during amplification of DNA trigger a color change of the PAPS dyes by sequestration of $Mn^{2+}$ from a dye:Mn complex. This is confirmed by demonstrating that addition of pyrophosphatase (Ppase) can prevent the color change. Additionally, EDTA mimics an amplification reaction by binding manganese with greater affinity than PAPS in the absence of an amplification reaction resulting in a color change.

FIG. 3A shows the chemical structures of 5-Bromo-PAPS and 5-Nitro-PAPS.

FIG. 3B shows the effects of degrading pyrophosphate by PPase or chelation of $Mn^{2+}$ by EDTA.

FIG. 3C shows the proposed mechanism of color transitions by PAPS dyes during LAMP amplification.

FIGS. 4A-4C show that 50 µM, 75 µM and 100 µM 5-Bromo PAPS provide similar results when tested against 0 µM, 50 µM, 75 µM, 100 µM or 150 µM manganese ions in the LAMP amplification reaction mix.

The colors of post-LAMP reactions and the real-time curves for each of the three concentrations of the PAPS dye are provided. The color coding for the real-time curves is the same as that of the labels for Mn2+ concentrations.

FIG. 4A shows results with 50 µM 5-Bromo-PAPS.

FIG. 4B shows results with 75 µM 5-Bromo-PAPS.

FIG. 4C shows results with 100 µM 5-Bromo-PAPS.

FIGS. 5A-5D show that a color change in the PAPS dye can readily be detected by the absorbance spectrum at peak maxima observed at 450 nm and 570 nm. As can be seen from the curves, a range of spectrums may be used on either side of the peak maxima to detect positive results. For example, wave lengths of 420 nm-500 nm instead of 450 nm and 520 nm-600 nm for 550 nm.

Figure 5A:
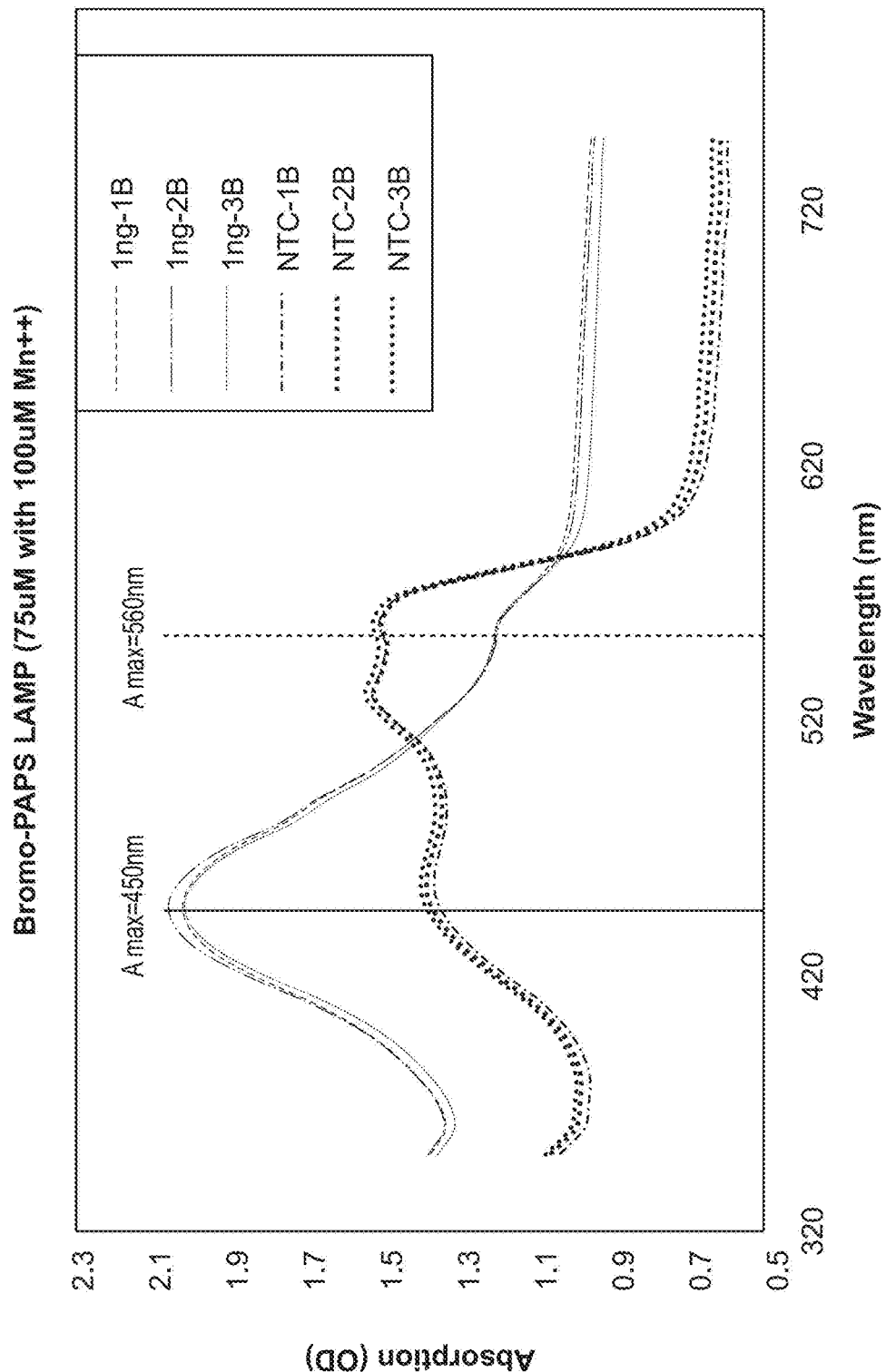

FIG. 5A shows the absorbance measured from 360 nm to 750 nm wavelength in reactions with 75 µM 5-Bromo-PAPS and 100 µM $Mn^{2+}$.

Figure 5B:
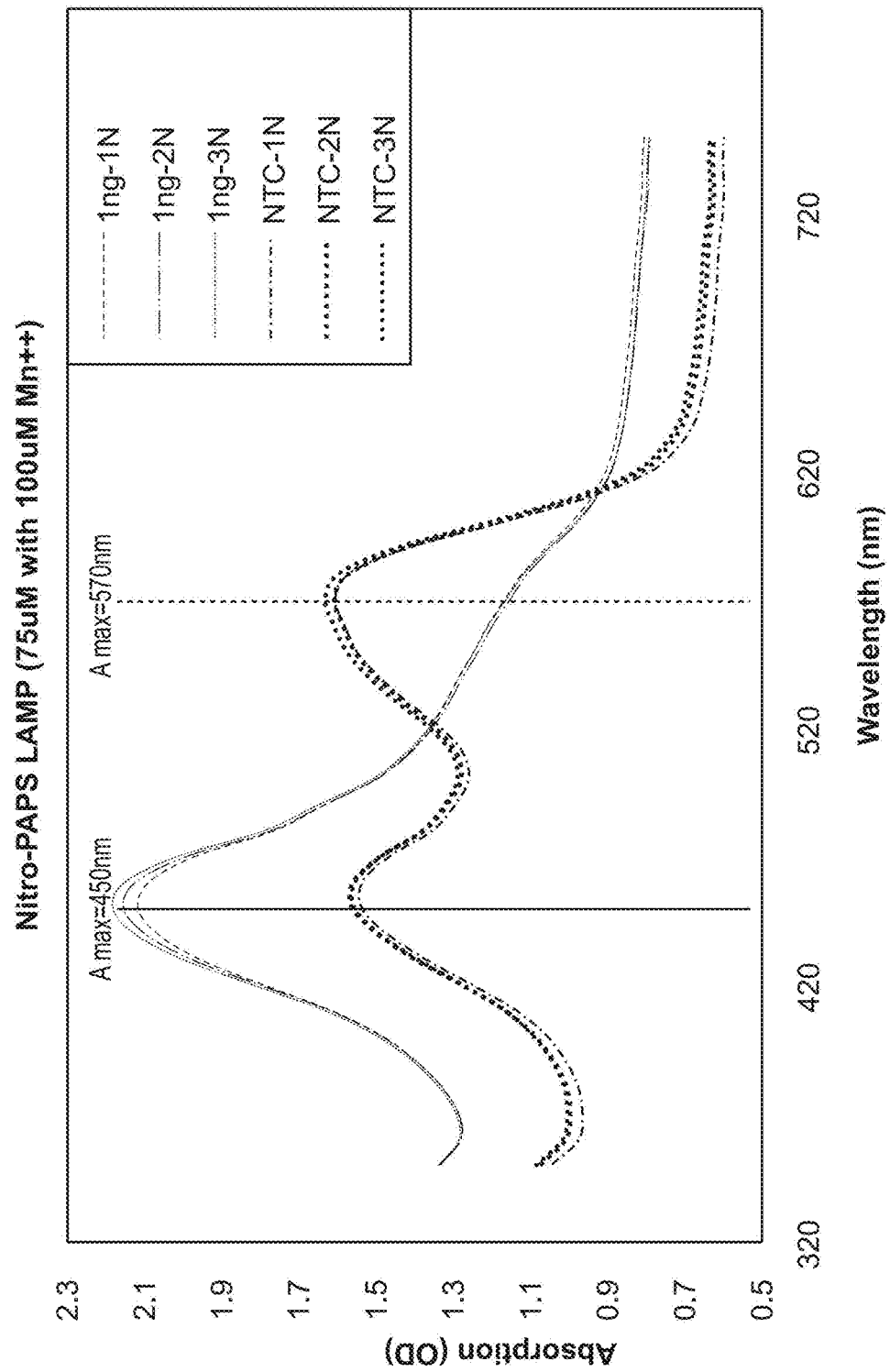

FIG. 5B shows the absorbance measured from 360 nm to 750 nm wavelength in reactions with 75 µM 5-Nitro-PAPS and 100 µM $Mn^{2+}$.

Figure 5C:
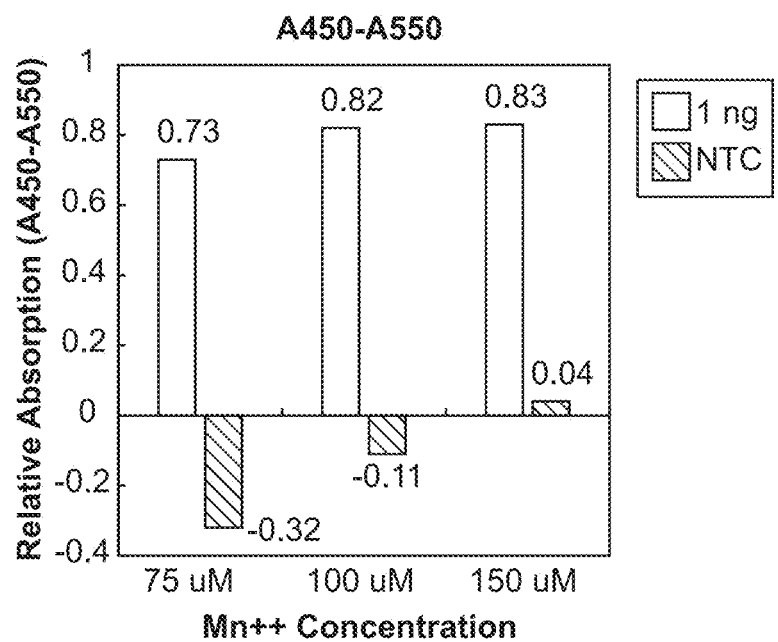

FIG. 5C shows the relative gain of absorbance at 450 nm and 550 nm in reactions with 75 µM 5-Bromo-PAPS and 75 µM-150 µM $Mn^{2+}$.

Figure 5D:
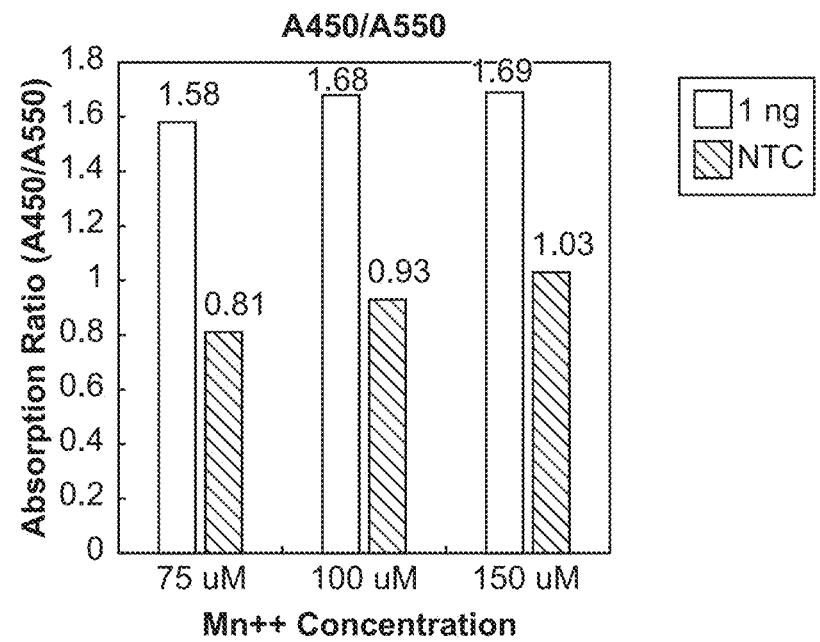

FIG. 5D shows the ratio of absorbance at 450 nm over 550 nm with 75 µM 5-Nitro-PAPS and 75-150 µM $Mn^{2+}$.

Figures 6A, 6B:
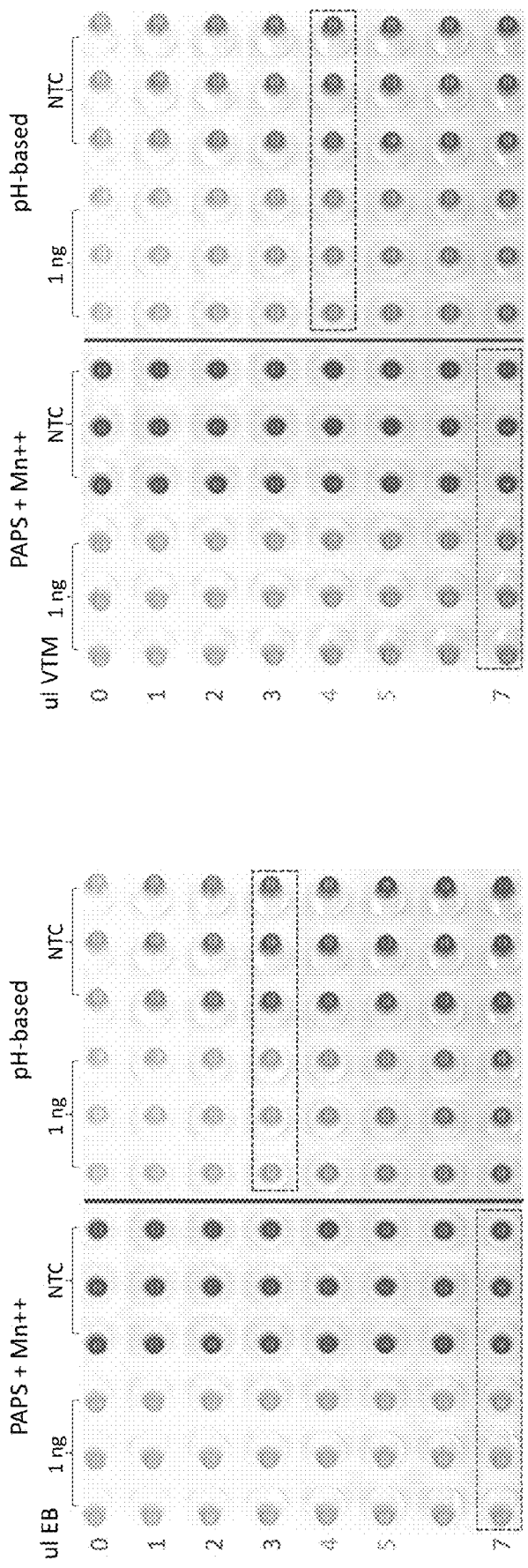

FIGS. 6A-6B show that in a comparison with pH based colorimetric LAMP, the PAPS dye LAMP tolerates more carryover solutions than pH based colorimetric LAMP. The carryover solutions shown here are from standard DNA purification column elution buffer (EB) or virus transport medium (VTM). Similar results are anticipated from carryover of body fluids such as saliva and nasal mucosa.

FIG. 6A shows that where samples 1-7 contain increasing volumes of a carryover buffer, the dotted rectangles show the difference in maximum tolerance to the amount of carryover of EB using the different color assays. Real-time curves (with color coding for different amounts of carryover solution) for LAMP reactions are provided beneath the colored wells (0-7 refers to 0-7 µL (0-28% v/v) of a typical nucleic acid purification column elution buffer (Qiagen EB, 10 mM Tris pH 8.5) in 25 µL LAMP reactions containing the PAPS reporter system).

FIG. 6B shows that where samples 1-7 contain increasing volumes of a carryover buffer, the dotted rectangles show the difference in maximum tolerance to the amount of carryover of VTM using the different color assays. Real-time curves (with color coding for different amounts of carryover solution) for LAMP reactions are provided beneath the colored wells.

FIGS. 7A-7D show that PAPS dyes are sensitive reporters of amplification using reverse transcription-LAMP (RT-LAMP), E1 primer set and as little as 10 copies of SARS-CoV-2 RNA.

Results for 24 reactions, each with approximately 10 copies of target RNA (A1-H3) and 8 NTC reactions (A4-H4) in the presence of 75 µM 5-Bromo-PAPS and 100 µM $Mn^{2+}$.

Figure 7B:
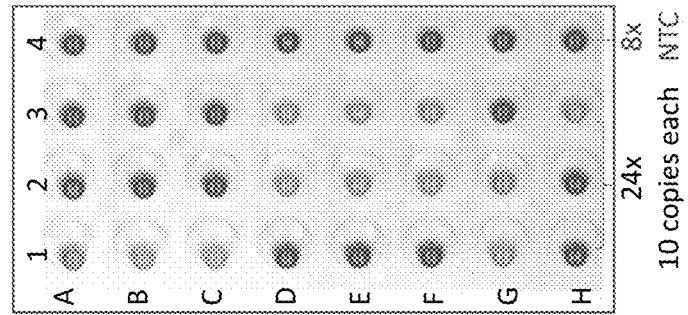
Figure 7A:
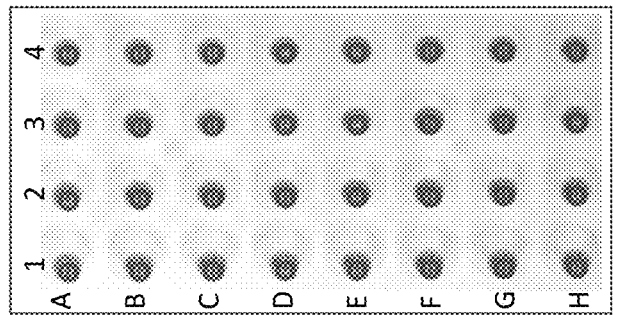

FIG. 7A shows the color of the reaction mix before amplification.

FIG. 7B shows the color if the reaction mix after amplification.

Figure 7C:
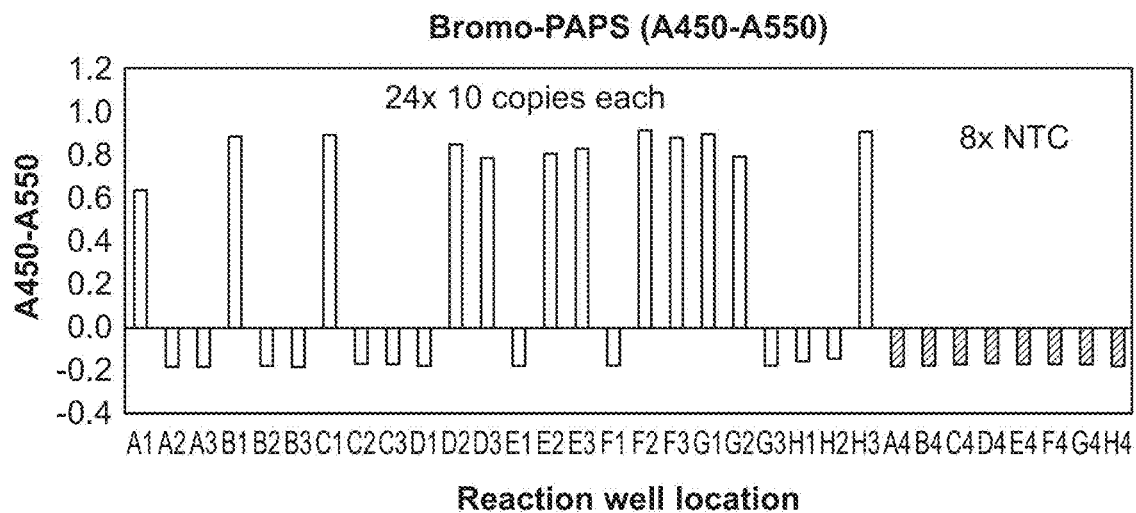

FIG. 7C shows the relative gain of absorbance at 450 nm and 550 nm.

Figure 7D:
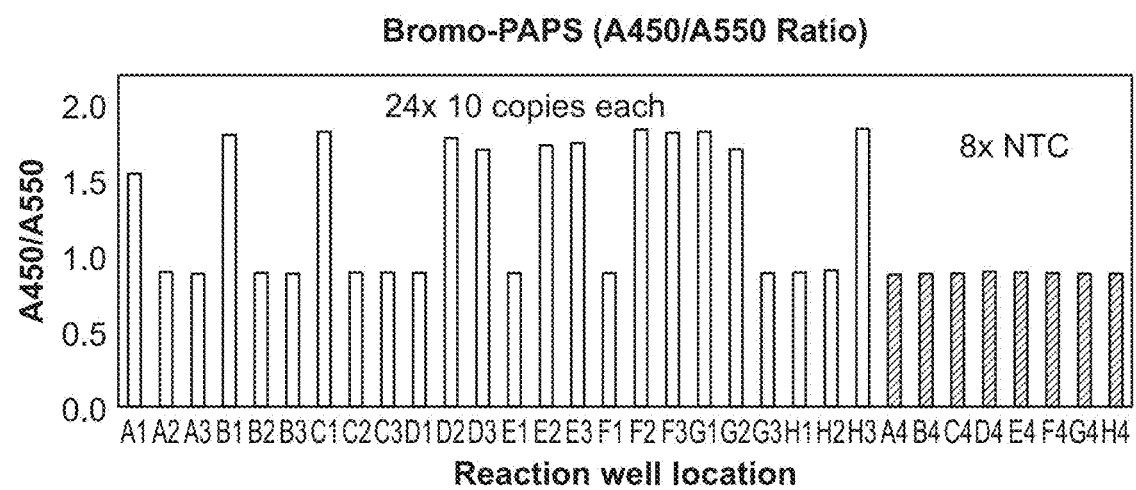

FIG. 7D shows the ratio of absorbance at 450 nm over 550 nm.

FIGS. 8A-8D shows that PAPS colorimetric detection can be effectively used for PCR of lambda DNA fragments of sizes in the range of 0.5 kb-5.0 kb and is tolerant of various buffers used in different PCR formulations. The results from triplicates samples (LongAmp® and OneTaq® (New England Biolabs, Ipswich, Mass.)) or duplicate samples (Q5® (New England Biolabs, Ipswich, Mass.)) in the presence of 50 µM Bromo-PAPS and 50 µM $Mn^{2+}$ are shown.

Figure 8A:
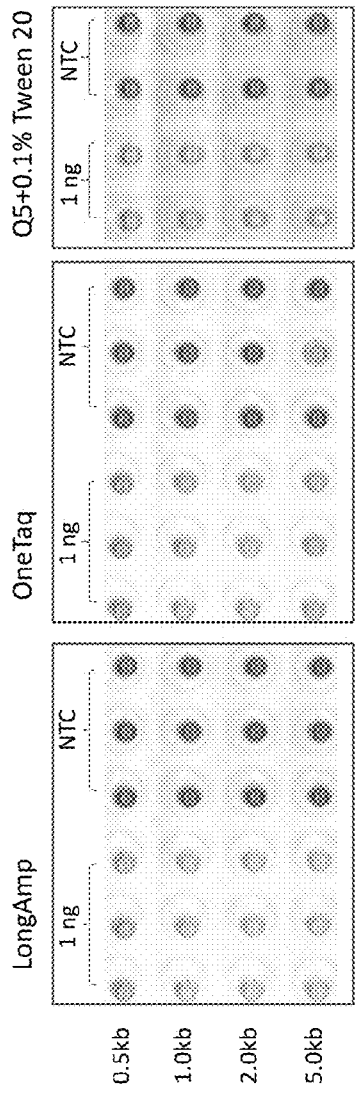

FIG. 8A shows the different end point dye colors for positive and negative samples (with and without 1 ng DNA template) after PCR with LongAmp Taq, OneTaq, and Q5 master mixes or non-template controls (NTC).

Figure 8B:
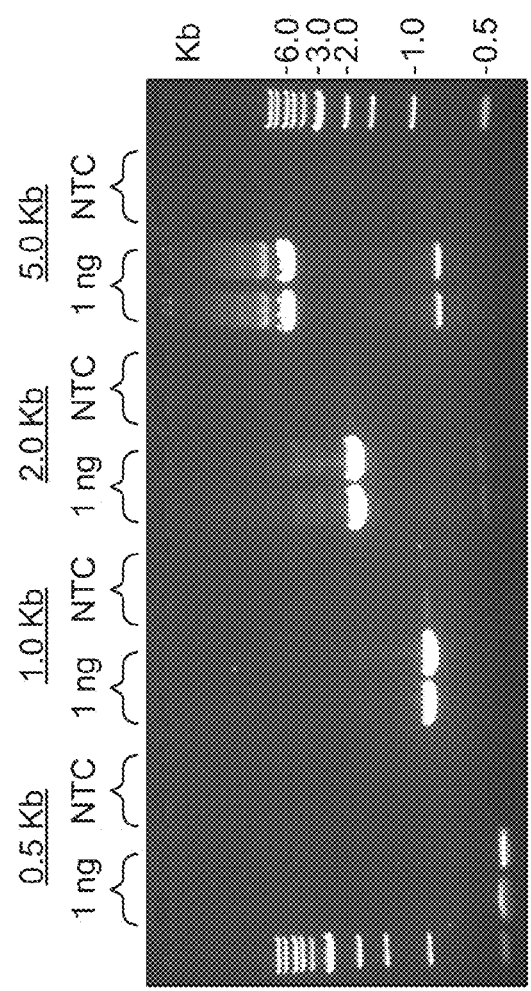

FIG. 8B shows the Q5 PCR products in FIG. 8A on agarose gels after electrophoresis in the presence of the dye where the DNA ranges in size from 0.5 kb, 1.0 kb, 2.0 kb and 5.0 kb.

Figure 8C:
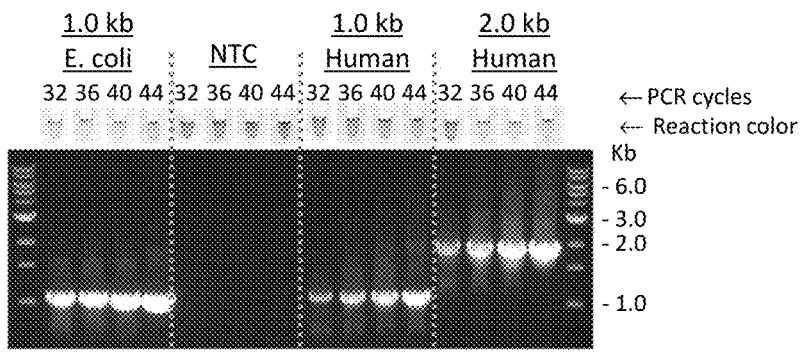

FIG. 8C shows the number of PCR cycles required for color change when amplifying DNA fragments with OneTaq PCR mix from *E. coli* and human genomes. The reaction color change is shown above the electrophoresed sample DNA.

Figure 8D:
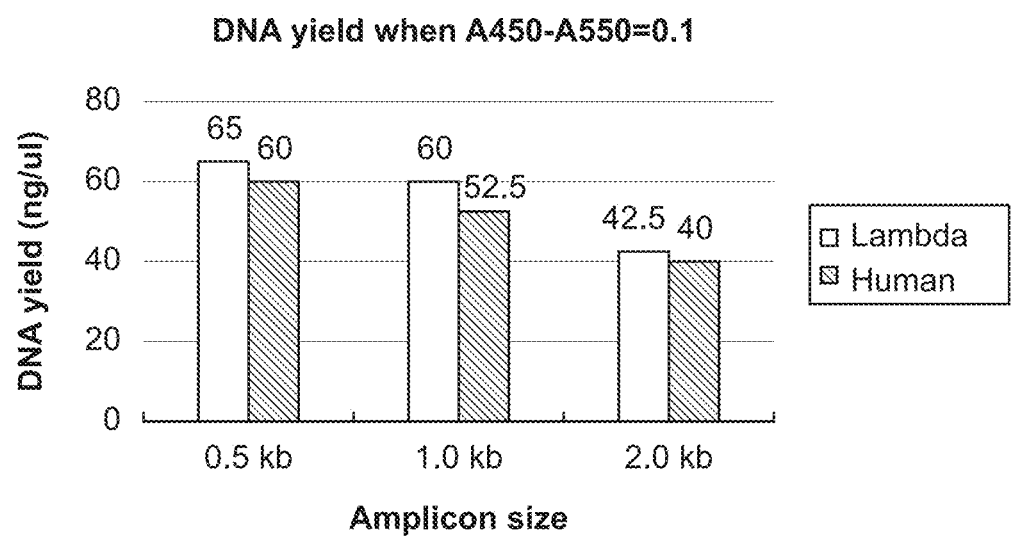

FIG. 8D shows the DNA yield (µg/µl) determined from A450-A550 ratios for variously sized lambda and human DNA after PCR using OneTaq.

FIGS. 9A-9D show that the colorimetric assay using PAPS dyes may be used directly for colony PCR to assess a target insert in a plasmid or the presence of the plasmid itself. Agarose gels are shown each with the corresponding colorimetric PCR assay above for *E. coli* colonies where four colonies are tested for plasmid I in FIG. 9A-9B containing a specific insert (1-4), four colonies are tested for plasmid II (1-4) in FIG. 9C and 8 colonies tested for plasmid I and II (FIG. 9D).

FIG. 9A shows optimization of annealing temperature for amplifying an 1172 bp fragment from plasmid I with purified plasmid DNA. The annealing temperature is shown above reaction tubes.

FIG. 9B shows the results of PCR with bacterial cells using specific primers recognizing a DNA insert (1172 bp) in a plasmid (plasmid I) in the presence of a colorimetric dye and comparing this to the same DNA obtained on a gel.

FIG. 9C shows the results of PCR with bacterial cells using specific primers recognizing a different DNA insert (1715 bp) in a plasmid (plasmid II) in the presence of a colorimetric dye and comparing this to the same DNA obtained on a gel.

FIG. 9D shows PCR with bacterial cells using primers recognizing both plasmid I (6136 bp) and II (5292 bp).

Figure 10A:
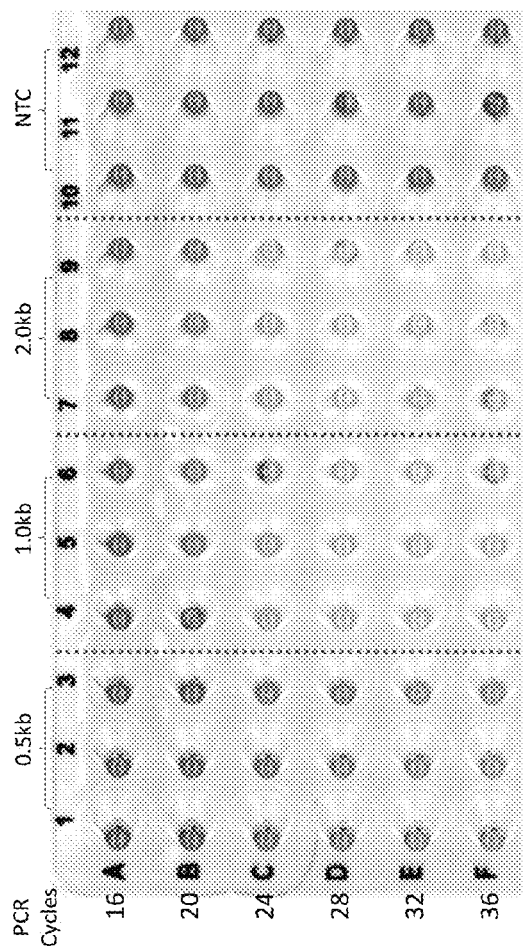
Figure 10C:
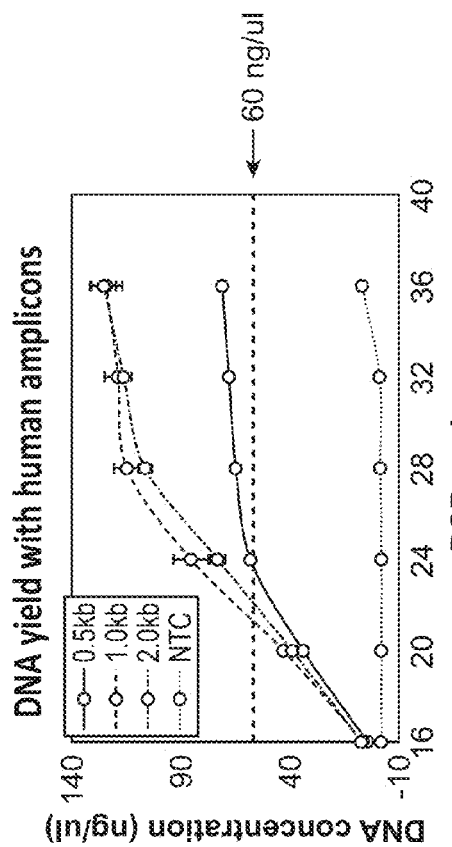
Figure 10B:
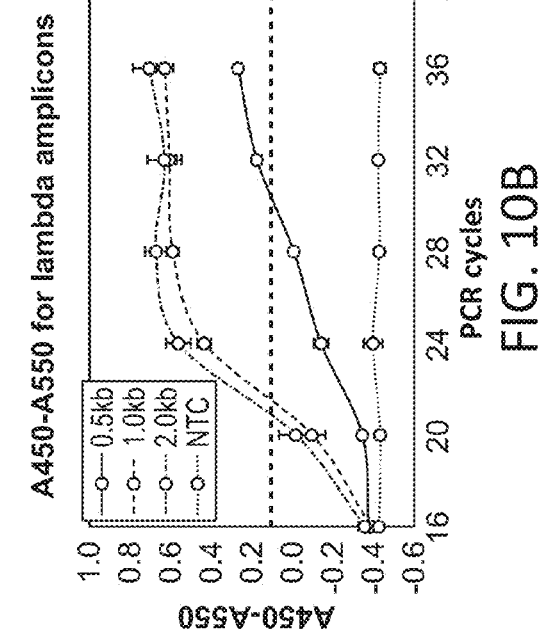

FIGS. 10A-10C show that the concentration of Lambda DNA in a sample can be determined by determining the number of cycles of PCR required to obtain a desired intensity of color change to yellow in the sample for a predetermined size of the amplicon.

FIG. 10A shows a time course of color changes of PAPS dye for triplicate PCR reactions after 16, 20, 24, 28, 32 and 36 PCR cycles using 0.5 kb, 1.0 kb and 2.0 kb Lambda DNA at a starting concentration of 1 ng lambda DNA (~1.9×10⁷ copies) and a NTC control reactions with primers for the 0.5 kb DNA in the absence of the template DNA.

FIG. 10B shows spectrophotometric scans of the samples from FIG. 10A at an absorbance at 450 nm and 550 nm, plotted against the PCR cycle numbers. An arbitrary threshold (dashed line) of 0.10 was drawn in the graph for visible color change perceivable by the naked eye.

FIG. 10C shows DNA yield in the reactions from FIG. 10A. The visual color change threshold (dashed line) corresponds to ~60 ng/µl amplicon yield in the PCR reactions.

Figure 11A:
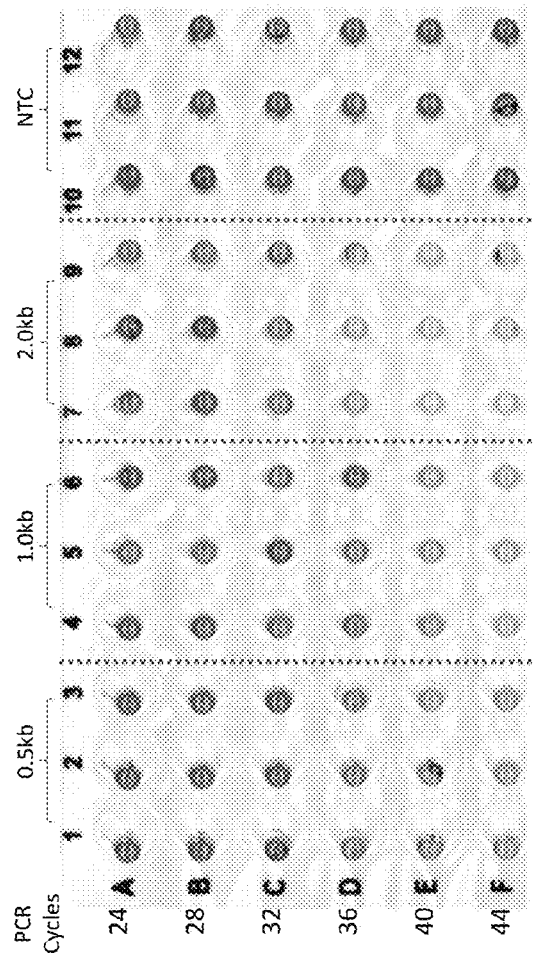
Figure 11C:
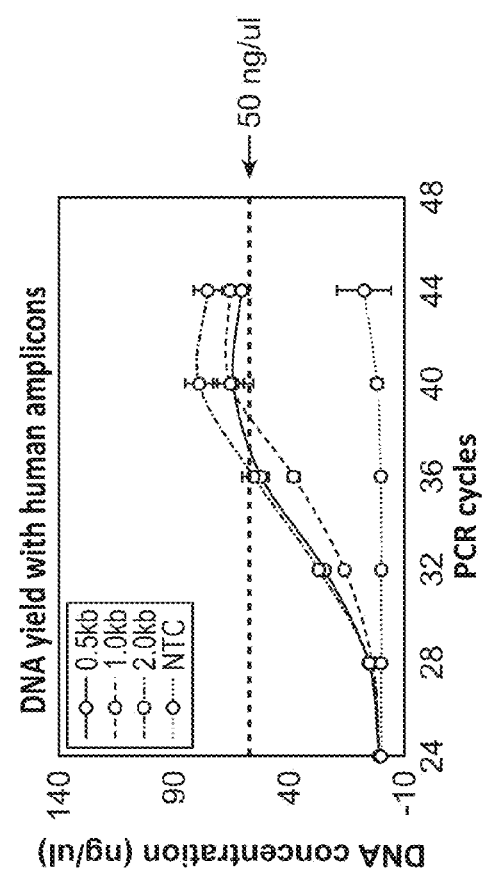
Figure 11B:
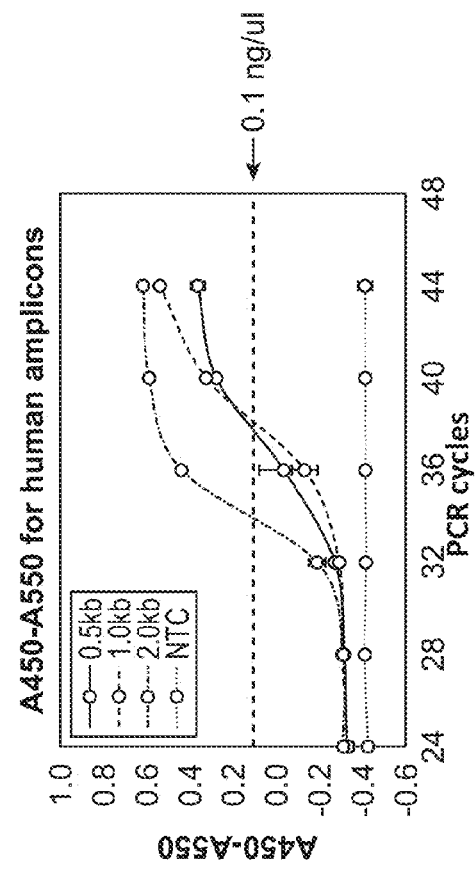
Figure 12A:
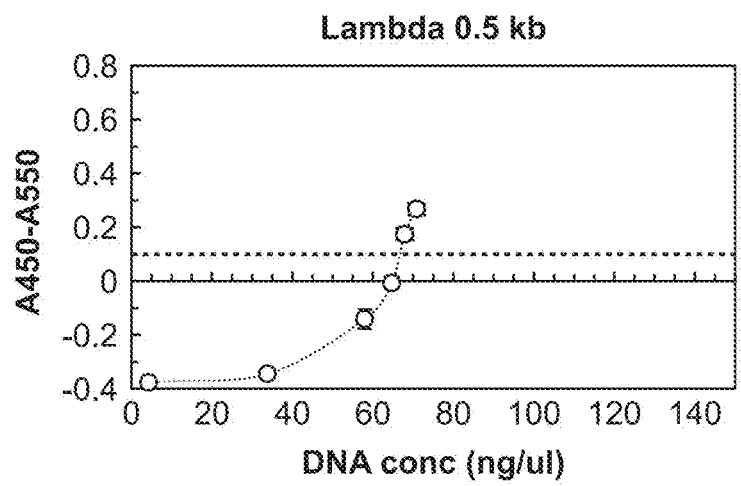
Figure 12B:
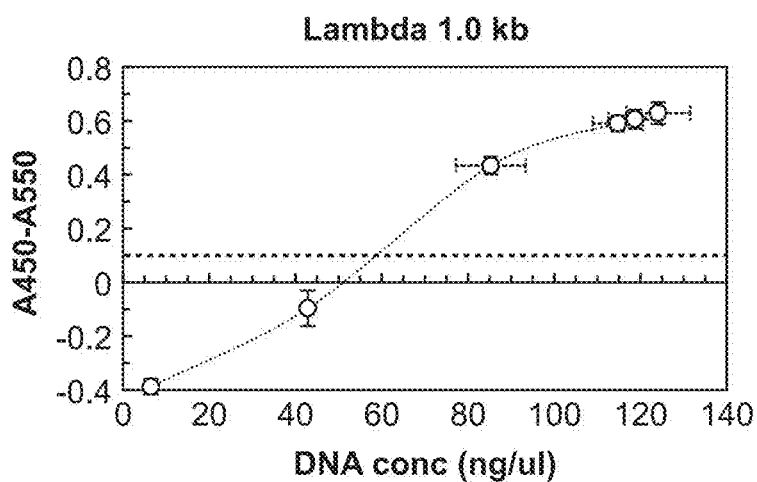
Figure 12C:
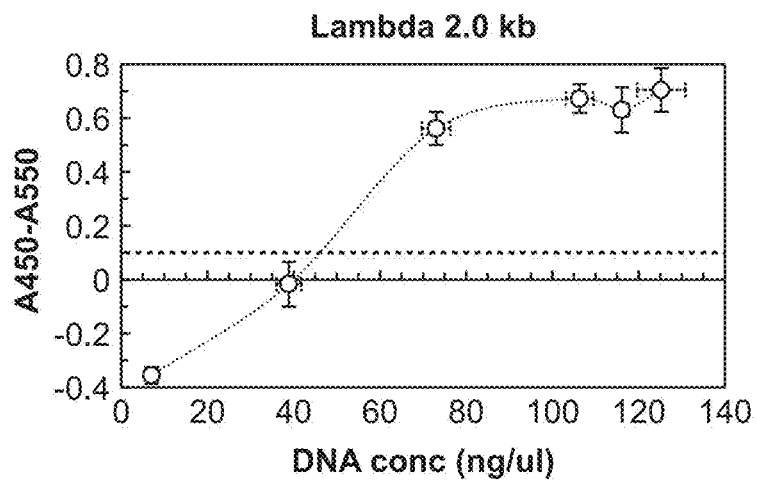
Figure 12D:
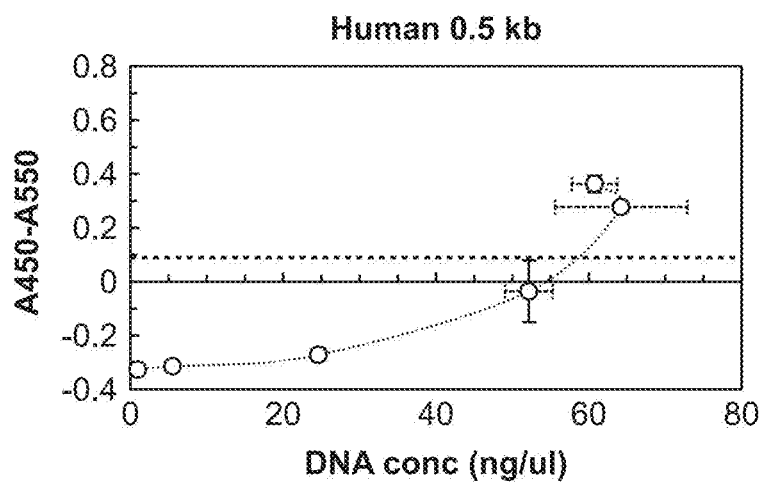
Figure 12E:
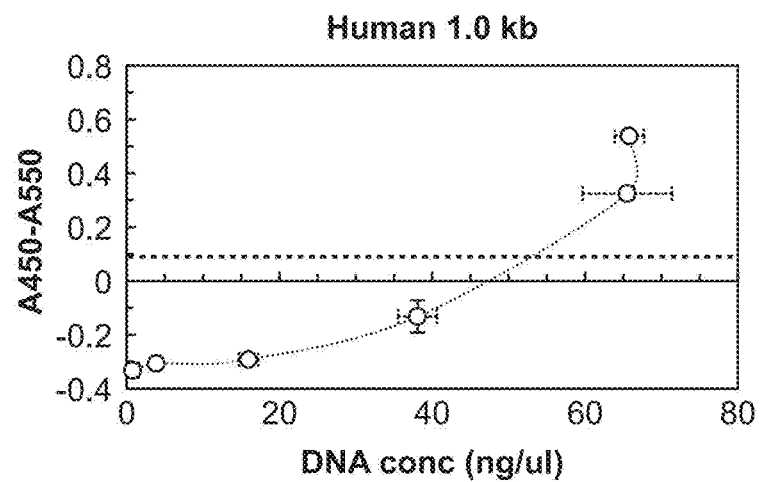
Figure 12F:
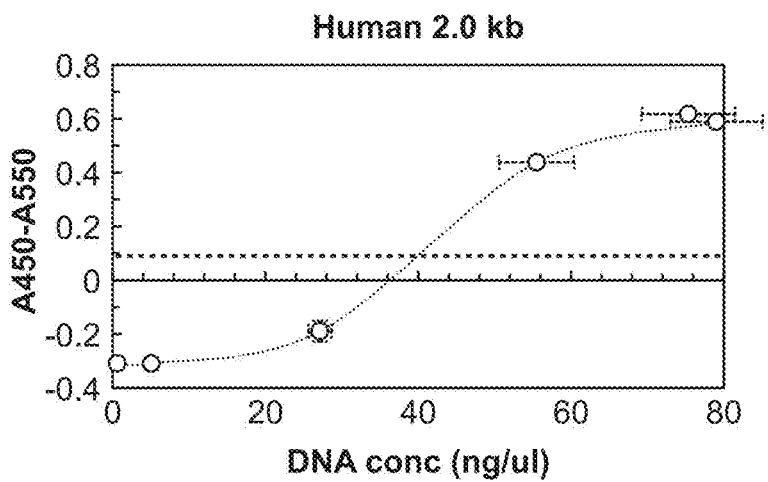

FIGS. 11A-11C show that the concentration yield of human DNA in a sample can be determined by PAPS dye color and correlated to the time course of PCR required to obtain a desired intensity of color change to yellow in the sample.

FIG. 11A shows a time course of color changes of PAPS dye for triplicate PCR reactions after 24, 28, 32, 36, 40 and 44 cycles using 0.5 k, 1.0 kb and 2.0 kb Human DNA at a starting concentration of 10 ng human DNA (~2,900 copies) and a NTC control reactions with primers for the 0.5 kb DNA in the absence of the template DNA. More PCR cycles were used with human versus lambda DNA because of the reduced template copy numbers.

FIG. 11B shows spectrophotometric scans of the samples from FIG. 11A at an absorbance at 450 nm and 550 nm, plotted against the PCR cycle numbers. An arbitrary threshold (dashed line) of 0.10 was drawn in the graph for visible color change perceivable by the naked eye.

FIG. 11C shows DNA yield in the reactions from FIG. 11A. The visual color change threshold (dashed line) corresponds to ~50 ng/µl amplicon yield in the PCR reactions.

FIGS. 12A-12F shows a useful correlation of color change with DNA yield in PCR reactions. The average absorbance gains (A450-A550) (Y-axis) of PCR reactions were plotted against DNA yield (X-axis) for lambda (A, B, C) and human (D, E, F) amplicons along 5 sampling points of PCR reactions (16, 20, 24, 28, 32 and 36 cycles for lambda amplicons and 24, 28, 32, 36, 40 and 44 cycles for human amplicons). The horizontal red dashed line corresponding to A450-A550 of 0.10, which is a point where a color change is perceivable by the naked eye. The DNA concentrations intercepted with this threshold were obtained as the DNA yield required to see color change and depicted in FIG. 8D.

Figure 13A:
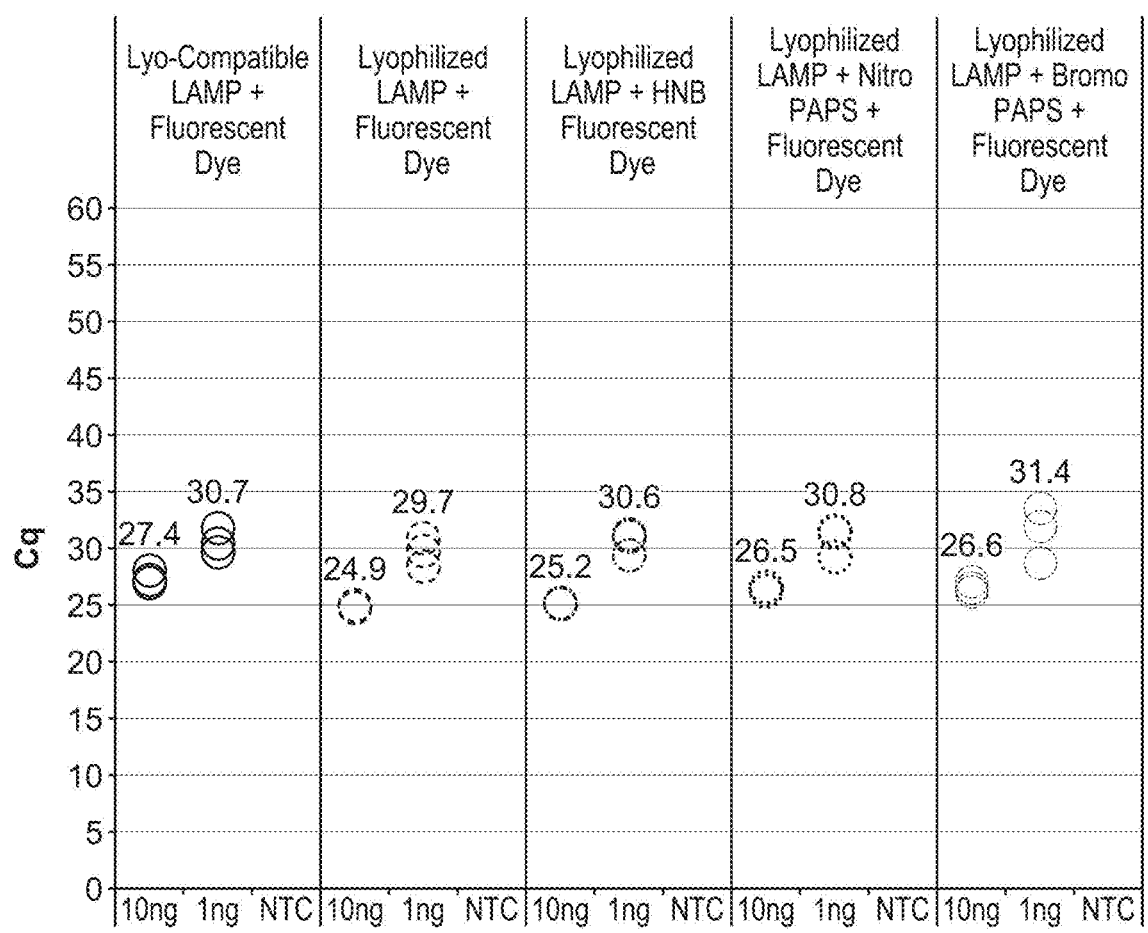
Figure 13B:
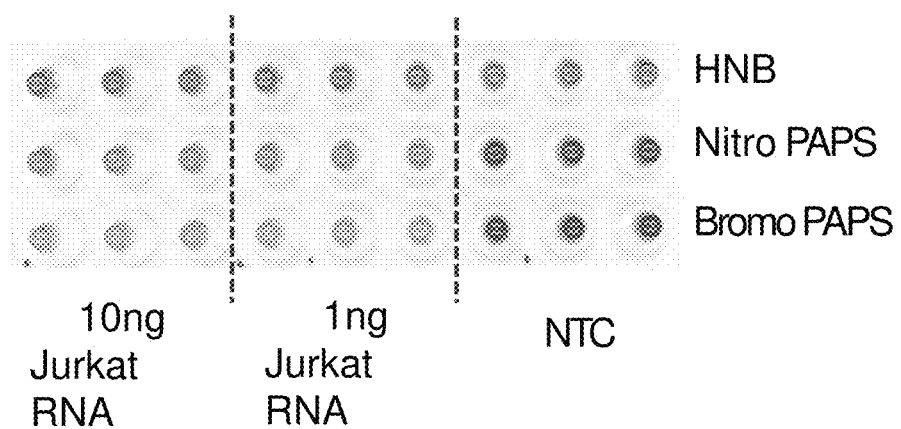

FIGS. 13A-13B show that the lyophilized PAPS dye RT-LAMP reaction provides similar results to lyophilized fluorescent dye LAMP and Lyo compatible fluorescent dye LAMP that has not been lyophilized, under the same reaction conditions using Jurkat RNA. However, when HNB dye is used in a lyophilized mixture, it fails to reveal a color change after the amplification reaction is completed.

DETAILED DESCRIPTION

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a," "an," and "the" include plural referents unless the context clearly dictates otherwise. For example, the term "a protein" refers to one or more proteins, i.e., a single protein and multiple proteins. The claims can be drafted to exclude any optional element when exclusive terminology is used such as "solely," "only" are used in connection with the recitation of claim elements or when a negative limitation is specified.

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which may be readily separated from or combined with the features of any of the other several embodiments without departing from the scope or spirit of the present teachings. Any recited method can be carried out in the order of events recited or in any other order which is logically possible.

Numeric ranges are inclusive of the numbers defining the range. All numbers should be understood to encompass the midpoint of the integer above and below the integer i.e. the number 2 encompasses 1.5-2.5. The number 2.5 encompasses 2.45-2.55 etc. When sample numerical values are provided, each alone may represent an intermediate value in a range of values and together may represent the extremes of a range unless specified.

In the context of the present disclosure, "non-naturally occurring" refers to a polynucleotide, polypeptide, carbohydrate, lipid, or composition that does not exist in nature. Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative).

All publications, patents, and patent applications mentioned in this specification are herein incorporated by reference to the same extent as if each individual publication, patent, or patent application was specifically and individually indicated to be incorporated by reference.

Dyes according to Formula 1 are a family of commercially available 4-(2-pyridylazo)aniline dyes that bind metals to form dye metal complexes and have been selected from a wide range of structures to provide an improvement to existing colorimetric detection of molecular biology reactions. This family of dyes are shown here to change color in the presence of pyrophosphate where the pyrophosphate is a product of an enzyme reaction. For example, pyrophosphate may be released by the conversion of nucleoside triphosphates (dNTPs or rNTPs, including ATP (the energy source)) sometimes referred to herein as NTPs, to nucleoside monophosphates by hydrolysis. Consequently, the dyes can be used as indicators that a specific enzyme reaction has occurred. In one embodiment, this family of dyes are used to determine reverse transcription of a target RNA and detect RNA and/or DNA by isothermal DNA amplification or PCR DNA amplification methods in a sample. It is desirable that color change of the dye that relies on a metal salt not interfere with the activity of the enzyme to perform the reaction. The observed improvements achieved with dyes of Formula 1 include an unambiguous difference in color between a sample in the presence of pyrophosphate (e.g., yellow) and a sample where no pyrophosphate is formed (e.g., red or purple brown) that also correspond to significantly different wavelengths for spectroscopic analysis.

The dye used in the present compositions and methods has a structure of Formula 1 (also named 4-(2-pyridylazo) aniline), having the structure shown below:

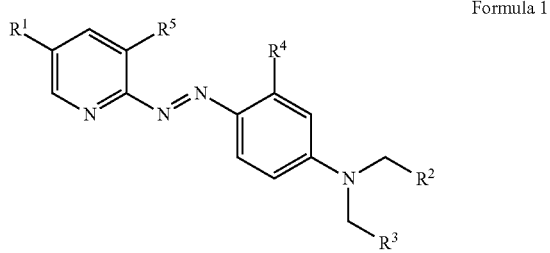

Formula 1 wherein:
R1 and R5 are each independently selected from the group consisting of H, halogen, nitro, cyano, sulfonic acid, carboxy, trifluoromethyl, trichloromethyl and tribromomethyl;
R2 and R3 are each independently a lower alkyl optionally comprising a terminal sulfonate group; and
R4 is H, OH or COOH.

In some embodiments, at least one of R1 and R5 is a halogen selected from F, Cl, Br and I, and R2 and R3 are each independently n-butyl, sec-butyl, isobutyl, tert-butyl, propyl, n-propyl, isopropyl, ethyl, or methyl and at least one of R2 and R3 comprises the terminal sulfonate group.

Figure 1A:
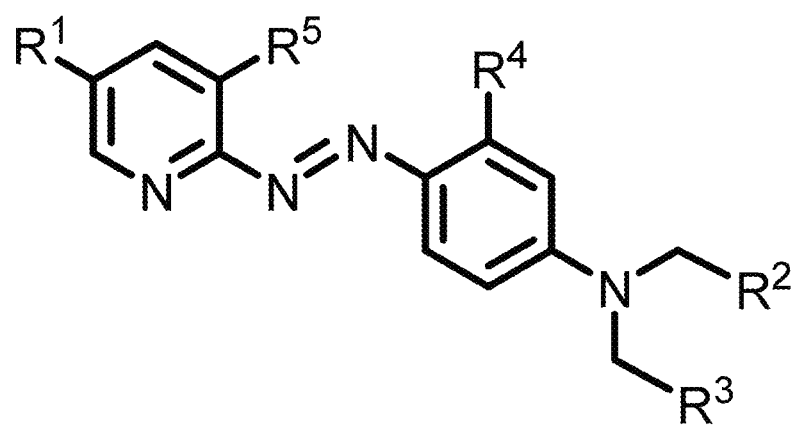
FIGS. 1A-1B shows the structures of a family of dyes identified as 4-(2-pyridylazo)aniline dyes (also referred to herein as pyridylazoaniline dyes) and represented by Formula 1 (FIG. 1A). Examples of this family of dyes show that these dyes perform better in colorimetric LAMP than other azo dyes that are not 4-(2-pyridylazo)aniline dyes (FIGS. 1C-1G).
Figure 1B:
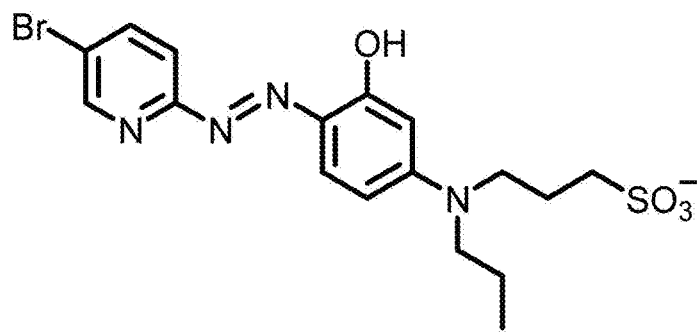
Figure 1B:
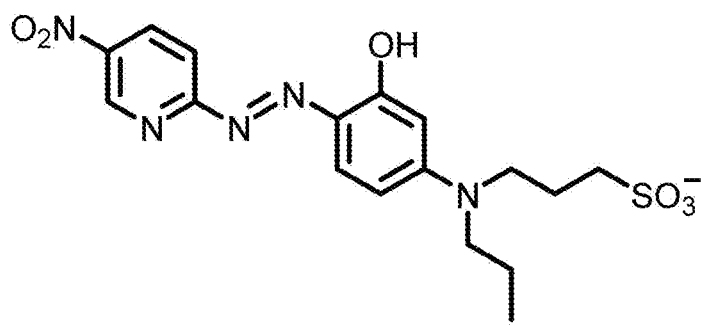
Figure 1B:
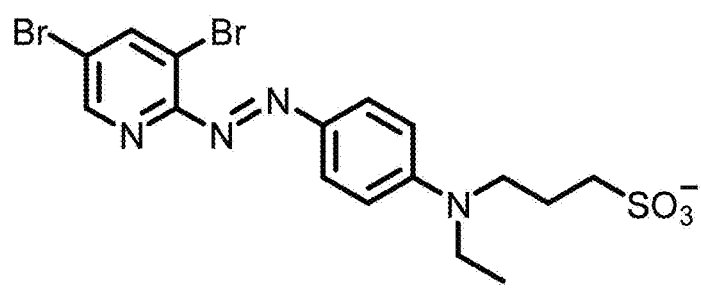

The dyes of Formula 1 exemplified in FIG. 1B were shown to be sensitive to production of pyrophosphates by hydrolysis of NTPs during amplification of nucleic acids. This sensitivity was identified using any of a plurality of amplification methods. These dyes enabled detection of relatively low concentrations of substrate and thus proved suitable for diagnostic detection of nucleic acids in the environment. The dyes of Formula 1 exemplified in FIG. 1B also enabled quantification of target nucleic acids and amplicon yield in purified or crude samples. These dyes were not adversely affected by pH changes nor by the presence of a variety of contaminants such as carry over buffers from columns, viral transport medium (VTM), body fluids such as saliva or nasal mucosa containing the nucleic acid, cell lysates, or from in vitro translation mixes. Other advantages include the ability of the dyes to be lyophilized with or without other reagents.

Colorimetric visual detection can enable simple diagnostic detection of nucleic acid amplification, using a visible readout for presence or absence of a DNA or RNA target of interest. The family of dyes characterized by Formula 1 are complexed to a metal ion, preferably $Mn^{2+}$ exemplified here. This family of dyes changes color in the reaction mix as a result of the amplification reaction that causes the removal of the metal ions from the dye. The selected metal ions such as manganese ions may be added to the dye in the form of a salt where the concentration of the salt is in the range of 2:1 to 1:2 dye to salt.

The color change is preferably binary and is the result of an optical density maximum at different distinct wavelengths of light correlated with a positive signal (amplified nucleic acid) or a negative signal (no amplification and therefore no target nucleic acid).

The DNA or RNA target of interest may be a nucleic acid from, for example, a pathogen, environmental sample, food or biopsy. The diagnostic detection of the nucleic acid may require large scale readout of plates in a diagnostic laboratory where the plates contain many samples for testing. In these circumstances, the use of a cheap effective spectrophotometer may be desirable that provides an optical density value for each sample at the selected positive and negative wavelengths where the data can be easily, accurately and cheaply processed by a computer to determine peak ratios or hues from the readout of the spectrophotometer.

Another application of colorimetric detection of amplification is the determination of the concentration of the amplified DNA by determining the ratio of peaks corresponding to the red color and the yellow color after amplification has occurred and optionally comparing these to peak heights before amplification. Determining yield of amplification may be of particular use in NGS library preparation, cloning and synthetic biology.

Alternatively, it may be desirable to perform a small numbers of diagnostic tests in the field or at point of care using for example, isothermal amplification. In these circumstances visual detection of target nucleic acid through a clear and unambiguous visual color change is desirable. In this circumstance it may be desirable to photograph the samples and perform image analysis using a cell phone camera or other means to quantify the results.

Another application of colorimetric detection of amplification is in molecular biology workflows using colony PCR, amplification to screen for correct assembly of a DNA molecule, typically by agarose gel electrophoresis. Colorimetric PCR using Formula 1 dye-metal complexes in the reaction mix shown here and in the examples can be used for rapid screening of these reactions, avoiding electrophoresis, saving time and increasing throughput.

In workflows where further processing or analysis is conducted on an in vitro or in vivo synthesized DNA or RNA, a colorimetric analysis ensures success of the amplification step before proceeding with secondary reactions.

Examples of such workflows include library preparation for next-generation sequencing, first strand cDNA generation by reverse transcriptase, and in vitro transcription by RNA polymerase to produce RNA. An additional use for these colorimetric dyes is for DNA sequencing reactions, where incorporated dNTPs produce a local concentration of pyrophosphate and the corresponding change in color is tied to incorporation of a specific sequence-determined nucleotide.

The sensitivity of the amplification assay for a target nucleic acid in the absence or presence of dye using a pyridylazoaniine dye-manganese complex was demonstrated to be similar. It was concluded therefore that the dye metal complex did not substantially adversely affect the activity of the DNA polymerase or reverse transcriptase.

The Formula 1 dyes and metal salt for use in a non-pH dependent colorimetric nucleic acid amplification assay were selected to preferably have two or more, three or more, five or more, or seven or more of the following features:

(a) Minimal adverse effect on the selected nucleic acid amplification reaction when included in the amplification reagent master mix;

(b) Minimal negative effect on sensitivity of the amplification reaction for detecting low amounts of nucleic acid;

(c) Minimal interference with primer binding to target nucleic acid and associated specificity of the reaction (d) Readily detectable color change direct resulting from nucleoside triphosphate hydrolysis;

(e) Distinctly different wavelengths associated with changes in the dye color;

(f) The dye produces a change in visible color in response to changes in concentration of a divalent metal that is not substantially affected by the presence of standard buffering agents or a pH between 7 and 9;

(g) The dye is commercially available;

(h) The dye is water soluble;

(i) The dye can be lyophilized.

In various enzyme dependent workflows that utilize NTPs, the dye-metal complex can be used as an indicator of nucleoside triphosphate hydrolysis. Enzymes that hydrolyze dNTPs or rNTPs include for example, DNA polymerase, RNA polymerase, reverse transcriptase, primase, ligase, helicase, nucleotide Ppase/phosphodiesterase, RNA decapping (RNA 5' pyrophosphohydrolase) and geranyl pyrophosphate synthase (used in terpene precursor production).

The dye-metal complex may be combined with any of these enzymes either separately or in combination with reagents where the reagents may be incorporated in a master mix in order to detect a reaction that generates pyrophosphates. Examples of such reactions include: amplification of nucleic acids to detect the presence of target nucleic acids; ligation of adaptors in NGS libraries; removal of pyrophosphates from capped RNA for various RNA workflows, measurement of RNA synthesis by RNA polymerase subject to selected promoters etc.

A master mix is a mixture of reagents for adding to a substrate to execute a reaction or series of reactions. The master mix may include all the reagents required for the reaction except for sample. Alternatively, a master mix may contain core reagents for a reaction but may not include all the reagents.

For example, a master mix for an amplification reaction may include a polymerase and dNTPs in a suitable buffer. If the master mix is for PCR, a reagent may be included such as an aptamer or antibody to block polymerase activity at room temperature. A pyridylazoaniline dye with manganese ions may also be included in the master mix or may be provided separately. Another master mix for amplification may include oligonucleotide primers for a specific target together with a DNA polymerase, dNTPs and optionally a pyridylazoaniline dyes with manganese ions. Another master mix may include a reverse transcriptase, DNA polymerase, dNTPs, optionally oligonucleotide primers and a pyridylazoalanine dye with manganese ions either separately or together. A master mix may contain the reagents at a concentration of at least 2×, 5× or 10× so that the master mix can be diluted into the sample resulting in a 1× solution.

Optional additional reagents in a master mix may include any of a helicase, a nicking endonuclease, guanidine hydrochloride, a detergent, a reducing agent, glycerol, a hygroscopic sugar, a buffer, a uracil DNA glycosylase or dUTP for preventing DNA carryover between reaction samples, and/or magnesium salts where the concentration of magnesium salts should be carefully titrated so as not to inhibit the removal of manganese from the dye in the presence of pyrophosphates while being of sufficient concentration to enable enzyme reactions that require magnesium ions.

The pyridylazoaniline dye metal complex may be stored separately or included in the master mix as a liquid formulation at cold temperatures such as 4° C., −20° C. or −70° C. or a temperature there between where the master mix may contain stabilizing agents such as at least 10% glycerol, preferably more than 20% glycerol such as at least 50% glycerol; detergents such as nonionic detergents, zwitterionic detergents, or anionic or cationic detergents.

The master mix may be freeze dried. As shown in FIG. 13, lyophilized master mix containing the pyridylazoaniline dye and manganese ions show similar LAMP activity to comparable formulations that are not lyophilized. This represents a significant advantage for extending shelf life or field use of the master mix to enable for example, point of care for infectious disease detection.

It has been demonstrated here that the reagents in the master mix do not substantially affect the sensitivity of the color change of a colorimetric dye following a target specific amplification. In certain circumstances according to the needs of the user, it may be desirable to combine a separate mix of pyridylazoaniline dye-metal complex with the master mix lacking the dye at the time of the reaction.

In one embodiment, a kit may contain the dye combined with an amplification master mix as a single reagent. In another embodiment, a kit may contain a container for the dye and a container for the master mix lacking the dye suitable for their combination in a reaction.

In one embodiment, a master mix is provided that is capable of amplifying nucleic acids when combined with a sample containing the nucleic acids. The pyridylazoaniline dye metal complex may be included in any master mix that is designed to accomplish amplification from a target DNA or RNA (in the presence of a reverse transcriptase) such as LAMP, polymerase chain reaction (PCR), strand displacement amplification (SDA/NEAR), helicase dependent amplification (HDA), multiple displacement amplification (MDA), rolling circle amplification (RCA), ligation mediated amplification, whole genome amplification (WGA), nucleic acid sequence-based amplification (NASBA), recombinase polymerase amplification (RPA), Cas-CrispR associated nonspecific amplification (CRISPR-NAS) and transcription mediated amplification (TMA). A master mix may be provided for first strand cDNA synthesis using a reverse transcriptase. A reverse transcriptase and an RNA polymerase may be included in the master mix for NASBA or TMA. The master mix may include an RNA polymerase but not a DNA polymerase or reverse transcriptase for in vitro transcription.

An amplification master mix typically includes one or more DNA and/or RNA polymerases. Examples of DNA polymerases include Taq polymerase or archaea polymerase or variants thereof. Variants of archaea polymerases include fusion proteins where the fusion may be between an archaea polymerase and a DNA binding domain that may have specific or non-specific binding properties. The DNA polymerase may be a strand displacing DNA polymerase such as a bacterial polymerase such as Bst or Bsu polymerase where variants include truncations at the N-terminal end or C-terminal end, or mutations there between. Examples of Bst variants are described in U.S. Pat. Nos. 8,993,298, 9,127,258, 9,157,073, EP 2751264, U.S. Pat. Nos. 9,447,445 and 9,963,687. DNA polymerases, RNA Polymerases or reverse transcriptases may also be phage polymerases such as Phi 29 DNA polymerase. Optionally, the polymerase is a fusion protein for example, a fusion protein between two different polymerase, between a polymerase and a DNA binding domain and/or binding affinity moiety. The polymerase may be immobilized on a solid substrate such as a bead or column.

The master mix may contain a reverse transcriptase and a DNA polymerase to enable detection of RNA target sequences where RNA is first converted to cDNA by the reverse transcriptase and then amplified by thermocycling (PCR) or isothermal amplification.

The master mix containing the pyridylazoaniline dye metal complex and one or more polymerases and/or reverse transcriptases may also include nucleoside triphosphates. The master mix may additionally include primers, adaptors, ligases, nicking endonucleases, restriction endonucleases, DNA glycosylases and/or exonucleases.

The master mixes containing the pyridylazoaniline dye metal complex may be lyophilized for room temperature storage. The master mix may contain a suitable sugar for lyophilization such as stachyose, trehalose or other suitable sugar for binding water molecules. In embodiments, the absorbance characteristics of the composition and the pyridylazoaniline dye-divalent metal complex is not substantially affected by the lyophilization process.

Although for workflow convenience, the pyridylazoaniline dye metal complex can be contained in an amplification master mix as described above, the pyridylazoaniline dye metal complex may be combined with any single component from the master mix in place of the whole master mix for convenience depending on the design of the assay.

Moreover, the pyridylazoaniline dye metal complex can be combined with a sample for testing or control sample, by addition in a separate step from the amplification master mix or portion thereof.

Preferably the dyes change their absorbance characteristics in response to loss of metal ions in the pyridylazoaniline-metal ion complex so that the dye-metal ion complex shows absorbance characteristic at one wavelength while the dye alone after release of the metal has absorbance characteristics at a second wavelength that is distinct and distinguishable from the first wavelength.

Pyridylazoaniline Dye-Metal Complex.

Working examples are provided herein for pyridylazoaniline compounds of Formula I (FIG. 1A) more specifically dyes described in FIG. 1B for PCR and for LAMP. These dyes have some if not all of the above described advantages (a)-(i). These molecules have phenolic and pyridylazo moieties with sulfonate groups that enhance water solubility. These dyes may form complexes with various metals such as Mn (II), Ca(II), Fe (II), Re (II), Co(III), Cr(III), Cu(II), Ni(II), Mn(II) and Zn(II) through the coordination of with oxygen of phenolic group and nitrogens of azo and pyridyl groups.

In preferred embodiments, manganese ions were selected for improved sensitive and binary color change (see FIG. 2A-2D). The color of these dyes without manganese or after sequestration of manganese ion is yellow. The metal ion dye complexes at the pH of amplification reactions are red and purple-brown for 5-Bromo-PAPS and 5-Nitro-PAPS, respectively.

In the presence of metal ions, a reagent dye-metal ion complex is formed with a modified absorption signal (e.g. red for 5-Bromo-PAPS). During nucleic acid amplification, pyrophosphate is released when dNTPs are converted to dNMPs. The liberated pyrophosphate competes for metal ion binding with the pyridylazoaniline dye. The result is the release of the metal ion from the dye and the binding of the metal ions to pyrophosphate. This restores the dye's original absorption signal (e.g. yellow for 5-Bromo-PAPS and 5-Nitro-PAPS).

Suitable dye to metal ratio were determined for 5-Bromo-PAPS and 5-Nitro-PAPS as shown in FIG. 4A-4C. Cationic detergent such as hexadecyltrimethylammonium (CP), cetyltrimethylammonium bromide (CTAB), Poly(diallyldimethylammonium chloride) (PDADMAC) may enhance the intensity of the signal for samples containing very low amounts of amplified nucleic acid.

Examples of pyridylazoaniline dyes in embodiments of the compositions described herein for use in amplification reactions comprising compounds of Formula I and including associated counterions are provided below.

In some embodiments, the R2 and R3 groups are each independently a lower alkyl group alkyl group with 1 to 10 carbon atoms (C1-C10), preferably from 1 to 4 carbon atoms (C1-C4), and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl. As noted above, one of R2 and R3 with have a terminal sulfonate group.

The mono- or bicyclic heteroaromatic group is selected from 2H-pyrrolyl, pyrrolyl, imidazolyl, benzimidazolyl, pyrazolyl, indazolyl, purinyl, 8-azapurinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinolinyl, pteridinyl, indolizinyl, 3H-indolyl, indolyl, isoindolyl, oxazolyl, isoxazolyl, thiazolyl, isothiazolyl, tetrazolyl, furazanyl, thienyl, furanyl, or benzo[d]pyrazolyl. More preferably the mono- or bicyclic heteroaromatic group is selected from the group consisting of pyridyl, e.g. 2-, 3- or 4-pyridyl, and thiazolyl; e.g. 2-thiazolyl.

Preferably the acyl group is lower alkylcarbonyl with 1 to 5 carbon atoms (C1-C5), e.g. acetyl, propionyl, n- or isopropylcarbonyl, or n-, iso- or tert-butylcarbonyl, or arylcarbonyl, e.g. benzoyl.

Preferred azo dyes according to structural Formula I are those compounds, including any associated counterions, which have one or more features selected from:

Preferred compounds according to structural Formula (I), including any associated counterions, are water-soluble azo dyes. Particularly preferred water-soluble azo dyes comprise a sulfonate group. Most preferred azo dyes are pyridylazo dyes which have an electron-withdrawing substituent at R1 position such as halogen, nitro, cyano, sulfonic acid, trifluoromethyl and trichloromethyl, most preferably bromo or nitro. Examples of preferred compounds according to structural Formula I are: 2-(5-bromo-2-pyridylazo)-5-[N-propyl-N-(3-sulfopropyl)amino]phenol disodium salt dihydrate (abbreviated as 5-Bromo-PAPS) and 2-(5-nitro-2-pyridylazo)-5-[N-propyl-N-(3-sulfopropyl)amino]phenol disodium salt dihydrate (abbreviated as 5-Nitro-PAPS).

In some embodiments, one or more preferred dyes according to structural Formula I are combined with one or more divalent metals selected from the group of Mg(II), Mn(II), Fe(II), Co(II), Ni(II), Cu(II), and Zn(II) where the metal ion is capable of being removed from the dye-metal complex in the presence of pyrophosphate. 5-Bromo-PAPS and 5-Nitro-PAPS were shown in FIG. 2A-2B to provide the desired visually detected binary color change (from red to yellow) in the presence of divalent manganese ions. In FIG. 2A-2B, manganese chloride was tested. However, manganese sulfate, nitrate, chloride, carbonate or any other salt of manganese would be expected to be effective in enabling a dye-manganese complex to form the observed red color and the manganese to be displaced by pyrophosphate to change the dye color to yellow. FIG. 3A-3C and FIG. 4A-4C illustrate that the concentration of divalent manganese salt was not critical to obtain the desired effect. This was observed at all concentrations of manganese salt tested, namely 50 μM-150 μM manganese chloride with 50 μM-5-Bromo-PAPS or 5-Nitro-PAPS. The ratio of manganese chloride to the dyes in FIG. 1B used in the examples was in the range of 1:2 manganese chloride to dye to 3:1 manganese chloride:dye. However it is expected that this range may be as much as 5:1 to 1:5 of manganese salt to dye.

In some embodiments a detergent, especially a cationic detergent (e.g., cetylpyridinium chloride (CPC), cetyltrimethylammonium bromide (CTAB), dodecyltrimethylammonium bromide (DTAB), and polydiallyldimethylammonium chloride (PDADMAC)) is further combined to provide further enhancement in colorimetric dye response. In some embodiments, two or more dyes producing the same or different visual color in the presence of a divalent metal are combined in the amplification buffer to provide further contrast in colorimetric detection. In other embodiments, two or more divalent metals are combined with a one or more dyes in the amplification buffer to provide further contrast in colorimetric detection. In some embodiments, the concentration ratio between a preferred dye and a divalent metal in the amplification buffer is varied to provide further contrast in colorimetric detection.

In some embodiments, the divalent metal forms insoluble precipitate with the pyrophosphate produced during an enzyme reaction such as amplification. Without wishing to be bound by theory, the formation of an insoluble metal pyrophosphate sequesters the metal away from dye-metal complexes resulting in a detectable hypsochromic shift. In some preferred embodiments, dye-metal complexes are not substantially affected by NTPs and any other phosphorylated species that may be present in the amplification buffer prior to the amplification reaction.

Uses of the Formula 1 Dye Metal Complexes in Colorimetric Amplification Assays.

The recent Covid pandemic has highlighted the need for easy, fast, sensitive and cost effective viral diagnostic tests for use in large scale (population testing) or small scale (personalized testing) that are capable of detecting viral nucleic acids from body fluids where the most readily accessible are nasal swabs and saliva. Formula 1 dye-metal complexes are here demonstrated to have the attributes required to achieve diagnostic tests such as these. Covid testing also has been used on environmental samples such as wastewater. Again, Formula 1 dye metal complex are a sensitive indicator that can be used with an amplification method of choice for use on site in real time.

Synthetic biology requires creating clones of bacterial containing the synthetic constructs in plasmids. Being able to rapidly and easily identify correctly assembled clones can expedite the process of discovery. Formula 1 dye metal complexes enable colony PCR to be rapidly performed without the need for gels.

Kits containing any of the above-described reagents are provided. In a kit the reagents may be mixed together, separate from one another, or any combination of the two. For example, a kit may contain an RNA or DNA polymerase, manganese salt, and a dye of formula 1 as described above. The kit may also contain NTPs, etc. and, in some case, instructions for use.

All publications, patents, and patent applications mentioned in this specification are herein incorporated by reference to the same extent as if each individual publication, patent, or patent application was specifically and individually indicated to be incorporated by reference including: US Provisional Ser. Nos. 63/263,361 and 63/263,364.

Embodiments

Embodiment 1. A composition comprising an enzyme that releases pyrophosphate from a substrate and a dye of Formula 1:

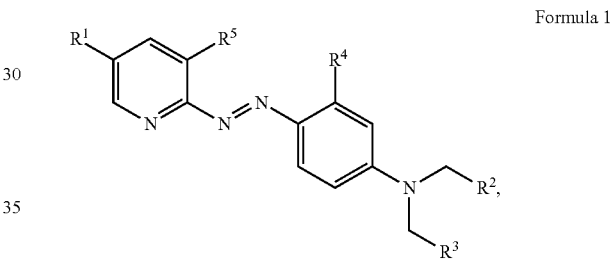

Formula 1 wherein:

R1 and R5 are each independently selected from the group consisting of H, halogen, nitro, cyano, sulfonic acid, carboxy, trifluoromethyl, trichloromethyl and tribromomethyl;

R2 and R3 are each independently a lower alkyl optionally comprising a terminal sulfonate group; and R4 is H, OH or COOH.

Embodiment 2. The composition of embodiment 1, wherein:

at least one of R1 and R5 is F, Cl, Br or I;

R2 and R3 are each independently n-butyl, sec-butyl, isobutyl, tert-butyl, propyl, n-propyl, isopropyl, ethyl, or methyl and at least one of R2 and R3 comprises the terminal sulfonate group.

Embodiment 3. The composition according to any prior embodiment, further comprising a divalent manganese salt ($Mn^{2+}$).

Embodiment 4. The composition according to any prior embodiment, wherein the composition comprises a divalent manganese salt wherein the molar ratio of the manganese salt to dye is greater than 1.

Embodiment 5. The composition according to any prior embodiment, wherein the composition further comprises one or more nucleoside triphosphates (NTPs) selected from rNTPs and dNTPs.

Embodiment 6. The composition according to any prior embodiment, wherein the molar ratio of NTPs to manganese salt is greater than 1.

Embodiment 7. The composition according to any prior embodiment, wherein the dye is 2-(5-Bromo-2-pyridylazo)-5-(N-propyl-N-sulfopropylamino)phenol (5-Br-PAPS) or 2-(5-Nitro-2-pyridylazo)-5-(N-propyl-N-sulfopropylamino) phenol (5-Nitro-PAPS).

Embodiment 8. The composition according to any prior embodiment, wherein the enzyme is a DNA polymerase, RNA polymerase, reverse transcriptase, primase, ligase, helicase, nucleotide Ppase/phosphodiesterase, RNA decapping enzyme (RNA 5' pyrophosphohydrolase) or geranyl pyrophosphate synthase Embodiment 9. The composition according to any prior embodiment, wherein the enzyme is a polymerase selected from a thermostable DNA polymerase, a strand displacing DNA polymerase, an RNA polymerase and a reverse transcriptase.

Embodiment 10. The composition according to embodiment 11, wherein the enzyme is Bst polymerase, Bsu polymerase, an archaeal DNA polymerase, Taq polymerase, or a variant thereof.

Embodiment 11. The composition according to any prior embodiment, wherein the composition is lyophilized or in an aqueous solution.

Embodiment 12. The composition according to any prior embodiment, further comprising a substrate for enzyme, wherein cleavage of the substrate by the enzyme results in production of pyrophosphate.

Embodiment 13. The composition according to any prior embodiment, further comprising a nucleic acid sample that contains a target nucleic acid and, optionally, primers.

Embodiment 14. The composition according to embodiment 14, wherein the sample is a sample from an animal subject.

Embodiment 15. The composition according to embodiment 14, wherein the sample is a clinical sample selected from the group consisting of: saliva, nasal mucosa, urine, tissue biopsy, and a cell scrape or an environmental sample selected from water, sewerage, soil and plants or animal material for use as food.

Embodiment 16. A method for detecting pyrophosphate, comprising:
(a) combining a manganese salt, an enzyme, a substrate for the enzyme that releases pyrophosphate when it cleaved by the enzyme, and a dye of Formula 1 produce a reaction mix;

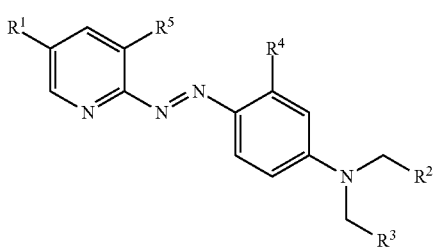

Formula 1 wherein:
R1 and R5 are each independently selected from the group consisting of H, halogen, nitro, cyano, sulfonic acid, carboxy, trifluoromethyl, trichloromethyl and tribromomethyl;
R2 and R3 are each independently a lower alkyl optionally comprising a terminal sulfonate group; and
R4 is H, OH or COOH;

(b) incubating the reaction mix under conditions by which the enzyme cleaves the substrate to produce pyrophosphate; and
(c) observing a change in color of the reaction mix, wherein the change in color indicates that pyrophosphate has been produced.

Embodiment 17. The method of embodiment 16, wherein the enzyme is a DNA polymerase, RNA polymerase, reverse transcriptase, primase, ligase, helicase, nucleotide Ppase/phosphodiesterase, RNA decapping enzyme (RNA 5' pyrophosphohydrolase) or geranyl pyrophosphate synthase.

Embodiment 18. The method of embodiment 16 or 17, wherein the substrate is an NTP.

Embodiment 19. The method of any of embodiments 16-18, wherein:
the reaction mix comprises a polymerase, rNTPs or dNTPs, the manganese salt, a template nucleic acid and the dye;
the reaction mix is incubated under conditions suitable for amplification of the nucleic acid; and
the change in color indicates that a product has been amplified.

Embodiment 20. The method of embodiment 19, wherein the reaction mix comprises an amplification mix for loop-mediated isothermal amplification (LAMP), polymerase chain reaction (PCR), strand displacement amplification (SDA), helicase dependent amplification (HDA), multiple displacement amplification (MDA), rolling circle amplification, ligation mediated amplification, whole genome amplification (WGA), nucleic acid sequence-based amplification (NASBA) or recombinase polymerase amplification (RPA) mix.

Embodiment 21. The method according to embodiment 19 or 20, wherein the reaction mix is a PCR reaction mix and the method comprises thermocycling the reaction mix.

Embodiment 22. The method according to embodiment 19 or 20, wherein reaction mix is a LAMP reaction mix and the method comprises incubating the reaction mix under isothermal conditions.

Embodiment 23. The method according to any of embodiments 16-22, wherein the color change in (c) is red to yellow wherein yellow indicates production of pyrophosphate.

Embodiment 24. The method according to any of embodiments 16-23, wherein the color change is detected by spectrophotometry, image analysis or by eye.

Embodiment 25. The method according to any of embodiments 16-24, wherein color change is a change in hue or a change in peak wavelength.

Embodiment 26. The method according to any of embodiments 16-25, wherein the change in color is detected by observing a change in a ratio of wavelength peak heights, before and after step (b).

Embodiment 27. The method according to embodiment 26, wherein the wavelength peak heights are in the range of 350 nm-620 nm, 430 nm-480 nm and/or 520 nm-620 nm.

Embodiment 28. The method according to any of embodiments 16-27, further comprising, determining the amount of nucleic acid substrate or the amount of amplicon by determining the number of thermocycles in a PCR amplification reaction for producing a predetermined ratio of wavelength peak height.

Embodiment 29. The method according to any of embodiments 16-28, wherein the dye is 2-(5-Bromo-2-pyridylazo)-5-(N-propyl-N-sulfopropylamino)phenol (5-Br-PAPS) or 2-(5-Nitro-2-pyridylazo)-5-(N-propyl-N-sulfopropylamino) phenol (5-Nitro-PAPS).

Embodiment 30. A kit comprising a polymerase, manganese salt, and a dye of formula 1

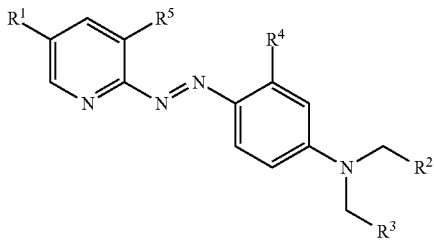

Formula 1 wherein:
R1 and R5 are each independently selected from the group consisting of H, halogen, nitro, cyano, sulfonic acid, carboxy, trifluoromethyl, trichloromethyl and tribromomethyl;
R2 and R3 are each independently a lower alkyl optionally comprising a terminal sulfonate group; and
R4 is H, OH or COOH.

EXAMPLES

Below are examples of specific embodiments for carrying out the present invention. The examples are offered for illustrative purposes only and are not intended to limit the scope of the present invention in any way.

Materials and Methods

Purchased chemical reagents: 5-Bromo-PAPS, 4-(2-pyridylazo)resorcinol), Eriochrome® Black T, $MnCl_2$, CaCl, $CuCl_2$, $ZnCl_2$, $FeSO_4$, $NiCl_2$, $ReCl_3$, and $CrCl_2$, were obtained from Sigma-Aldrich (St. Louis, Mo.), 5-Nitro-PAPS from Dojindo Molecular Technologies (Rockville, Md.), and hydroxynaphthol blue from Acros Organics. All molecular reagents were obtained from New England Biolabs (Ipswich, Mass.), unless otherwise noted.

For screening metal sensing dyes and metal ions, 25 μL LAMP reactions were performed in triplicate using WarmStart® LAMP Kit (DNA & RNA) (New England Biolabs, Ipswich, Mass.) with a lambda DNA primer set (Tanner et. al., Biotechniques 58(2), 59-68 (2015)) using 1 ng lambda DNA or NTC. Dyes and metal ions were diluted to 25× concentration and then mixed into LAMP reactions to 1× concentration before incubation. The reactions were incubated at 65° C. on a Bio-Rad CFX96™ Real-Time PCR instrument (Bio-Rad Laboratories, Hercules, Calif.) with readings performed at 15 second intervals (108 cycles, ~40 minutes). Before and after incubation, the color of each reaction was recorded by scanning with an office scanner (Epson® Perfection Photo Scanner V600 (Epson, Los Alamitos, Calif.)). The absorbance of each reaction was measured on a SpectraMax® M5 Microplate Reader (Molecular Devices, San Jose, Calif.). Thermostable Inorganic Ppase was added (1 Unit) to 25 μL LAMP reactions in the test of pyrophosphate requirement. For comparing tolerance of carryover solutions, the elution buffer (10 mM Tris, pH8.5) from a QIAquick® PCR Purification Kit (Qiagen, Hilden, Germany) and VTM (BD™ Universal Viral Transport medium, (Becton Dickinson, Franklin Lakes, N.J.)) were used. The pH-based colorimetric LAMP reactions were performed with WarmStart Colorimetric LAMP 2× Master Mix (DNA & RNA) following the product recommendations. For RT-LAMP, the SARS-CoV-2 E1 and N2 primer sets were used along with synthetic SARS-CoV-2 RNA from Twist Bioscience (Twist Synthetic SARS-CoV-2 RNA Control 2) (Twist Bioscience, South San Francisco, Calif.) diluted to ~10 copies/μL in the presence of 10 ng/μL Jurkat total RNA.

Colorimetric detection of PCR amplification was performed in 25 μL reactions by including 50 μM PAPS dye and 50 μM $Mn^{2+}$ into reactions with either LongAmp Taq 2× Master Mix or OneTaq 2× Master Mix with Standard Buffer. The same concentrations of PAPS dye and $Mn^{2+}$ were added to Q5 High-Fidelity 2× Master Mix and supplemented with Tween 20 to a final concentration 0.1%. The primer pairs for amplifying lambda DNA fragments had the same forward primer 5' CCTGCTCTGCCGCTTCACGC (SEQ ID NO:1) with different reverse primers to create different product lengths. The reverse primers are shown below:

5' TCCGGATAAAAACGTCGATGACATTTGC (SEQ ID NO:2); product length 0.5 kb;
5' GATGACGCATCCTCACGATAATATCCGG (SEQ ID NO:3); product length 1 kb;
5' CCATGATTCAGTGTGCCCGTCTGG (SEQ ID NO:4); product length 2.0 kb; and
5' CGAACGTCGCGCAGAGAAACAGG (SEQ ID NO:5); product length 5.0 kb.

For amplifying 1-2 kb fragments from *E. coli* and 0.5 kb-2 kb human genomic DNA, reactions were performing using LongAmp Hot Start Taq 2× Master Mix with 50 μM Bromo-PAPS, either 25 or 50 μM $Mn^{2+}$, and either 1 ng *E. coli* DNA (~200,000 copies) or 10 ng Jurkat cell DNA (~2,900 copies).

The primer sequences for the 1 kb *E. coli* fragment are:
Forward: 5' CCTGGATCCAGATGCAGTAATACCGC (SEQ ID NO:6);
Reverse: 5' TCCGAGGATGGTATTCGTCATG (SEQ ID NO:7).

The primer sequences for the 0.5 kb human fragment are:
Forward: 5' GGGGCACCTTCTCCAACTCATACT (SEQ ID NO:8);
Reverse: 5' CGAGCTACCACGCAGACATCAACC (SEQ ID NO:9).

The primer sequences for the 1 kb human fragment are:
Forward: 5' GGGGCACCTTCTCCAACTCATACT (SEQ ID NO:10);
Reverse: 5' CCTCATTTGGGGAGGGGTTATCT (SEQ ID NO:11).

The primer sequences for the 2 kb human fragment are:
Forward: 5' GAAGAGCCAAGGACAGGTAC (SEQ ID NO:12);
Reverse: 5' CCTCCAAATCAAGCCTCTAC (SEQ ID NO:13).

DNA yield for PCR reaction was determined using Quant-iT™ PicoGreen® dsDNA Assay Kits (Thermo Fisher Scientific, Waltham, Mass.).

For colony PCR, a small portion of an *E. coli* colony was transferred using a pipette tip to 15 μL water. 1 μL of the bacterial suspension was used for each PCR reaction with LongAmp.

Similar conditions were used for amplifying the 6,136 bp and 5,292 bp fragments, except that the extension time at 65° C. was adjusted to 5 minutes. 5 μL of each PCR product was analyzed by electrophoresis on 1% agarose gel along with a Quick-Load® 1 kb DNA Ladder (New England Biolabs, Ipswich, Mass.).

The compounds shown in FIG. 1B were tested though data mainly for 5-Bromo-PAPS are provided in the examples in the interest of brevity.

Results

Metal binding dyes in combination with various metal ions were screened in fully buffered (20 mM Tris) reactions. Bright colors were observed with pyridylazoaniline dyes, 5-Bromo-PAPS and 5-Nitro-PAPS before LAMP when complexed with $Cu^{2+}$, $Zn^{2+}$, $Fe^{2+}$ and $Ni^{2+}$ but not with $Ca^{2+}$, $Cr^{2+}$ and $Re^{3+}$. However, the observed colors were substantially unchanged after LAMP except for $Mn^{2+}$ ions. $Mn^{2+}$ changed the color of 5-Bromo-PAPS and 5-Nitro-PAPS from red to yellow at the end of LAMP (FIGS. 2A-2D) and PCR amplification for positive samples (FIG. 8A-8C). A pyridylazo dye 4-(2-pyridylazo)resorcinol (PAR) that had a different core structure also changed color in response to LAMP amplification in the presence of $Mn^{2+}$, but the color contrast was much less pronounced from yellow to orange after amplification (FIG. 1E). Two other dyes, HNB and EBT, which have been used as indicators for LAMP amplification based on $Mg^{2+}$ sensing, had their coloring almost completely quenched by addition of $Mn^{2+}$ (FIGS. 1F and 1G).

The hypothesis that the pyridylazoaniline dye complexes with $Mn^{2+}$ to give a red color but is displaced by the Pyrophosphate (PPi) produced during amplification to form insoluble manganese(II) pyrophosphate, thereby restoring the dye original yellow color (FIG. 3C) was tested with 5-Bromo PAPS (FIG. 3A). Inorganic Ppase added to the pyridylazoaniline dye complexed with $Mn^{2+}$ that converts the PPi generated by DNA polymerization to inorganic monophosphate (Pi) abrogated the red-to-yellow color change due to amplification (FIG. 3B). Furthermore, high concentrations of EDTA resulted in red-to-yellow color change immediately, independent of amplification, showing that EDTA chelates the $Mn^{2+}$ more strongly than the pyridylazoaniline dye (FIG. 3B).

Concentration ranges of 5-Bromo-PAPS dyes (50-100 μM) and $Mn^{2+}$ (50 μM-150 μM) were tested to determine whether the ratio was critical. FIGS. 4A-4C show that this was not the case and all ratios tested were effective. Using real-time fluorescence, at these concentrations, neither PAPS dyes nor manganese ions were observed to cause any significant suppression of the LAMP reaction. All combinations provided a high-contrast visual difference between positive and NTC reactions and reliable visual detection of LAMP amplification. 75 μM PAPS dye with 100 μM $Mn^{2+}$ was used in subsequent studies for convenience.

The absorbance spectrum shift of PAPS dyes in completed LAMP reactions is another useful indicator of a positive amplification reaction. In positive reactions, the absorbance at 450 nm significantly increased while the absorption around 550 nm decreased considerably. These shifts of absorbance peaks could be used to quantitatively determine positive reactions in objective automated measurement systems. Two approaches to quantitatively measure positive reactions are shown in FIGS. 5A-5D: using the relative absorbance difference between 450 nm and 550 nm (FIG. 5C) or the ratio between these peaks (FIG. 5D). Both methods provided easily distinguishable readouts of positive and negative reactions. In addition to end point analysis, the absorbance of these two peaks could be measured in real time and applied to determine amplification results, similarly to what was shown for the pH-based colorimetric method used in the high-throughput Color Health COVID-19 colorimetric LAMP assay.

Having determined factors that affect color change with the pyridylazoaniline dyes, the pyridylazoaniline-based detection method was then used to determine the sensitivity of detection of synthetic SARS-CoV-2 RNA using RT-LAMP. 24 reactions were performed with an input of approximately 10 copies of viral RNA per reaction, which is below the limit of detection of a commercially available kit based on a pH-dependent dye (~50 copies, SARS-CoV-2 Rapid Colorimetric LAMP Assay Kit (New England Biolabs, Ipswich, Mass.). At this low level of nucleic acid, both positive and negative reactions could be detected by eye (FIG. 7A-7D) suggesting that this was the limit of visual detection for this assay. Out of the 24 reactions, 12 showed color change as positive LAMP reaction after a 40 minute incubation. These were also determined to be positive by real-time fluorescence detection. The other 12 reactions showed no color change and matched the 8 NTC reactions which had no amplification as confirmed by real-time detection. By plotting the relative absorption change at 450 nm and 550 nm (FIG. 7C) or the ratio between them (FIG. 7D), values for positive reactions consistently showed a large difference from those of negative and NTC reactions, providing an unambiguous identification criterion for virus-specific amplification.

To determine whether pyridylazoaniline dyes and $Mn^{2+}$ affected RT-LAMP detection sensitivity, tests were performed with two primer sets for SARS-CoV-2, with or without guanidine hydrochloride (GuHCl) (Table 1). Each condition was tested with 24 replicates of ~10 copies of SARS-CoV-2 RNA. Comparing the number of positives across the different conditions, 75 μM PAPS dye and 100 μM $Mn^{2+}$, added individually or in combination, had no impact on the detection sensitivity. Moreover, not only was GuHCl compatible with the reaction conditions, but also slightly increased the detection sensitivity.

TABLE 1

| Sensitivity of RT-LAMP in the presence of 75 μM Bromo-PAPS and/or 100 uM Mn++ | | | | |
|---|---|---|---|---|
| | E1700 only | | E1700 + 5-Bromo-PAPS | |
| Primer and GnCl | No Mn++ | 100 uM Mn++ | No Mn++ | 100 uM Mn++* |
| N2 | 6/24 | 5/24 | 4/24 | 7/24 |
| N2 (+GnCl) | 10/24 | 8/24 | 9/24 | 9/24 |
| E1 | 7/24 | 6/24 | 7/24 | 5/24 |
| E1 (+GnCl) | 12/24 | 12/24 | 13/24 | 12/24 |
| N2 + E1 (+GnCl) | 14/24 | 21/24 | 19/24 | 21/24 |

*The results for reactions with both 5-Bromo-PAPS and Mn++ were determined based on color change and the results were identical to that by real time monitoring.

Advantages of the pyridylazoaniline colorimetric reporter system over pH-based detection, were demonstrated by testing the tolerance of various buffer carryover (FIG. 6A-61B). For example 0 μL-7 μL (0-28% v/v) of a typical nucleic acid purification column elution buffer (Qiagen EB, 10 mM Tris pH 8.5) in 25 μL LAMP reactions with the PAPS reporter system did not interfere with the color change nor inhibit the LAMP reaction. However, with pH-based colorimetric detection, positive and negative reactions displayed much less contrast even with 3 μL-4 μL of the elution buffer. Similarly, 0 μL-7 μL of VTM was tolerated by PAPS-based colorimetric detection, whereas clear visual contrast was only achieved up to 4 μL of VTM with the pH-based system. Tolerance in quantitative measurement systems, e.g., absorbance, is likely even higher than what is clear by eye. These results demonstrate that PAPS-based detection permits the use of higher volumes of buffering agents, and thus overcomes a critical limitation associated with pH-based colorimetric LAMP.

Pyridylazoaniline dyes exemplified by 5-Bromo-PAPS dyes are visual reporters for PCR reactions. 0.5 kb-5.0 kb long fragments from lambda DNA were amplified using PCR in the presence of 50 μM 5-Bromo-PAPS and 50 μM Mn2+ with three commercial PCR master mixes (FIG. 8A) using standard PCR conditions recommended by the manufacturer. Before PCR cycling, all reactions displayed a red color as it was seen in the LAMP mix. After the completion of PCR, reactions containing a template DNA changed color from red to yellow, while the no-template control reactions remained red. Samples with color change matched exactly with those of successful standard PCR amplification, as determined by agarose electrophoresis (FIG. 8B). The results showed that the PAPS dyes were generally compatible with standard PCR mixes. A benefit of PAPS based detection is that an overlay of mineral oil of the samples is not required.

The robustness and sensitivity of PAPS-based colorimetric PCR detection was determined by amplifying DNA fragments from *E. coli* and human genomes for 32-44 cycles and compared the color change with the yield of specific product bands by electrophoresis (FIG. 8A-8D). For a 1.0 kb *E. coli* fragment using 1 ng of input genomic DNA template (~200,000 copies), the reaction color changed to yellow in less than 32 PCR cycles. For a human fragment of the same size using 10 ng of genomic DNA (~2,900 copies), 40 cycles were used to obtain the desired color change.

When the human fragment size increased to 2 kb, the cycle numbers required for the color change reduced to 32-36 cycles. These results indicated that the color change depended on the amount of DNA produced, corroborating the product yields visualized by gel electrophoresis.

The relationship between visual color change and DNA yield was quantified visually and by absorbance spectra (FIGS. 10A-10C, FIG. 11A-11C, FIG. 12A-12F). Colorimetric PCR reactions was performed with a range of cycle numbers to amplify low (human genomic DNA, ~2900 copies) and high (lambda DNA, ~$1.91 \times 10^7$ copies) copy number templates, including for each 0.5 kb, 1.0 kb and 2.0 kb amplicons. The reactions were checked for visual color change, measured for both absorbance and DNA yield. The absorbance change (A450-A550) indeed correlated with DNA yield, and could be detected at least 4 cycles before the visible color chan. As expected, high copy number of templates for the lambda amplicons required fewer PCR cycles to accumulate similar amount of DNA and change color than that of low copy number human templates. The DNA yield at a point when color change starting to be perceivable by the naked eye were very similar across all amplicons of both lambda and human in the range of 40-65 ng/ul.

A further example of workflow improvement enabled by colorimetric PCR, can be observed for colony PCR using 5-Bromo-PAPS (FIG. 9A-9D). Colony PCR is routinely used to identify colonies carrying a correct plasmid DNA assembly, directly from a small amount of *E. coli* cells. It typically requires manual gel electrophoresis to confirm the product presence and size. Cloned plasmids transformed in *E. coli* were chosen for analysis by PCR using PAPS. The best annealing temperature for each primer pair was determined according to routine practice using purified plasmid DNA in the presence of 5-Bromo-PAPS and $Mn^{2+}$ (FIG. 9A). Eight *E. coli* colonies, were analyzed by PCR-four each from two different plasmids. The selected primer pairs were either unique for the first 4 colonies (FIGS. 9A and 9B), unique for the second 4 colonies (FIG. 9C), or common for both (FIG. 9D). The resulting PCR reactions changed color only when there was a correct target plasmid and matched perfectly with the specific bands detected by agarose electrophoresis. The PCR results for detecting positive colonies using PAPS was at least as good as obtained with standard agarose gel electrophoresis using a much simpler workflow that avoided gels.

What is claimed is:

1. A composition, comprising; an enzyme that releases pyrophosphate from a substrate, a manganese ion ($Mn^{2+}$) and a dye of Formula 1:

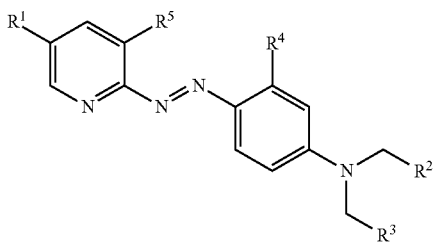

Formula 1 wherein:
R1 and R5 are each independently selected from the group consisting of H, halogen, nitro, cyano, sulfonic acid, carboxy, trifluoromethyl, trichloromethyl and tribromomethyl;
R2 and R3 are each independently a lower alkyl optionally comprising a terminal sulfonate group; and
R4 is H, OH or COOH.

2. The composition of claim 1, wherein:
at least one of R1 and R5 is F, Cl, Br or I;
R2 and R3 are each independently n-butyl, sec-butyl, isobutyl, tert-butyl, propyl, n-propyl, isopropyl, ethyl, or methyl and at least one of R2 and R3 comprises the terminal sulfonate group.

3. The composition according to claim 1, wherein the composition comprises a manganese salt, wherein the molar ratio of the manganese salt to dye is greater than 1.

4. The composition according to claim 1, wherein the composition further comprises one or more nucleoside triphosphates (NTPs) selected from rNTPs and dNTPs.

5. The composition according to claim 4, wherein the molar ratio of NTPs to manganese salt is greater than 1.

6. The composition according to claim 1, wherein the dye is 2-(5-Bromo-2-pyridylazo)-5-(N-propyl-N-sulfopropylamino)phenol (5-Br-PAPS) or 2-(5-Nitro-2-pyridylazo)-5-(N-propyl-N-sulfopropylamino)phenol (5-Nitro-PAPS).

7. The composition according to claim 1, wherein the enzyme is selected from the group consisting of a DNA polymerase, RNA polymerase, reverse transcriptase, primase, ligase, helicase, nucleotide pyrophosphatase (Ppase)/phosphodiesterase, RNA decapping enzyme (RNA 5' pyrophosphohydrolase) and geranyl pyrophosphate synthase.

8. The composition according to claim 1, wherein the enzyme is a polymerase selected from the group consisting of a thermostable DNA polymerase, a strand displacing DNA polymerase, an RNA polymerase and a reverse transcriptase.

9. The composition according to claim 7, wherein the enzyme is a DNA polymerase selected from the group consisting of Bst polymerase, Bsu polymerase, an archaeal DNA polymerase, Taq polymerase, or a variant thereof.

10. The composition according to claim 1, wherein the composition is lyophilized or in an aqueous solution.

11. The composition according to claim 1, further comprising a substrate for the enzyme, wherein cleavage of the substrate by the enzyme results in production of pyrophosphate.

12. The composition according to claim 1, further comprising a nucleic acid sample that contains a target nucleic acid and, optionally, primers.

13. The composition according to claim 12, wherein the sample is a sample from an animal subject.

14. The composition according to claim 12, wherein the sample is a clinical sample selected from the group consisting of: saliva, nasal mucosa, urine, tissue biopsy, and a cell scrape or an environmental sample selected from the group consisting of water, sewerage, soil and plants or animal material for use as food.

15. A method for detecting pyrophosphate, comprising:
(a) combining a manganese salt, an enzyme, a substrate for the enzyme that releases pyrophosphate when it is cleaved by the enzyme, and a dye of Formula 1 produce a reaction mix;

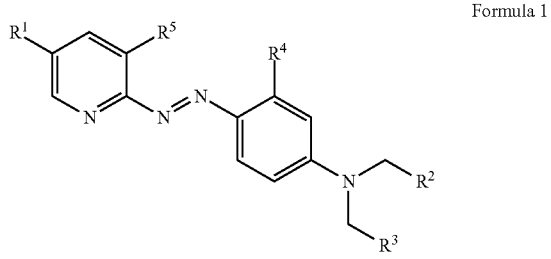

Formula 1 wherein:
R1 and R5 are each independently selected from the group consisting of H, halogen, nitro, cyano, sulfonic acid, carboxy, trifluoromethyl, trichloromethyl and tribromomethyl;
R2 and R3 are each independently a lower alkyl optionally comprising a terminal sulfonate group; and
R4 is H, OH or COOH;
(b) incubating the reaction mix under conditions by which the enzyme cleaves the substrate to produce pyrophosphate; and
(c) observing a change in color of the reaction mix, wherein the change in color indicates production of pyrophosphate.

16. The method of claim 15, wherein the enzyme is selected from the group consisting of a DNA polymerase, an RNA polymerase, a reverse transcriptase, a primase, a ligase, a helicase, a nucleotide pyrophosphatase (Ppase)/phosphodiesterase, an RNA decapping enzyme (RNA 5' pyrophosphohydrolase) and a geranyl pyrophosphate synthase.

17. The method of claim 15, wherein the substrate is an NTP.

18. The method of claim 15, wherein:
the reaction mix comprises a polymerase, rNTPs or dNTPs, the manganese salt, a template nucleic acid and the dye;
the reaction mix is incubated under conditions suitable for amplification of the nucleic acid; and
the change in color indicates that a product has been amplified.

19. The method of claim 18, wherein the reaction mix comprises an amplification mix for loop-mediated isothermal amplification (LAMP), polymerase chain reaction (PCR), strand displacement amplification (SDA), helicase dependent amplification (HDA), multiple displacement amplification (MDA), rolling circle amplification, ligation mediated amplification, whole genome amplification (WGA), nucleic acid sequence-based amplification (NASBA) or recombinase polymerase amplification (RPA) mix.

20. The method according to claim 18, wherein the reaction mix is a PCR reaction mix and the method comprises thermocycling the reaction mix.

21. The method according to claim 18, wherein reaction mix is a LAMP reaction mix and the method comprises incubating the reaction mix under isothermal conditions.

22. The method according to claim 15, wherein the color change in (c) is red to yellow wherein yellow indicates production of pyrophosphate.

23. The method according to claim 15, wherein (c) further comprises detecting the color change by spectrophotometry, image analysis or by eye.

24. The method according to claim 15, wherein (c) further comprises detecting the color change by a change in hue or a change in peak wavelength.

25. The method according to claim 15, wherein the change in color is detected by observing a change in a ratio of wavelength peak heights, before and after step (b).

26. The method according to claim 25, wherein the wavelength peak heights are in the range of 350 nm-620 nm, 430 nm-480 nm and/or 520 nm-620 nm.

27. The method according to claim 18, further comprising, determining the amount of nucleic acid substrate or the amount of amplicon by determining the number of thermocycles in a PCR amplification reaction for producing a predetermined ratio of wavelength peak height.

28. The method according to claim 15, wherein the dye is 2-(5-Bromo-2-pyridylazo)-5-(N-propyl-N-sulfopropylamino)phenol (5-Br-PAPS) or 2-(5-Nitro-2-pyridylazo)-5-(N-propyl-N-sulfopropylamino)phenol (5-Nitro-PAPS).

29. A kit comprising a polymerase, manganese salt, and a dye of formula 1

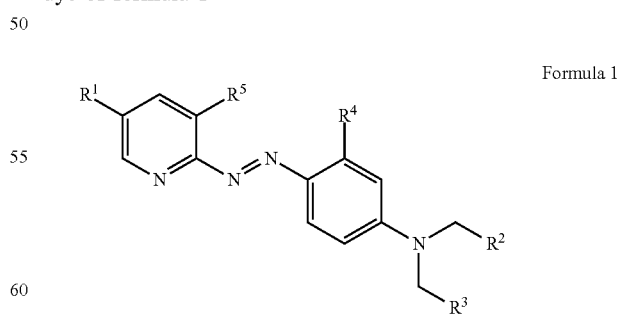

Formula 1 wherein:
R1 and R5 are each independently selected from the group consisting of H, halogen, nitro, cyano, sulfonic acid, carboxy, trifluoromethyl, trichloromethyl and tribromomethyl;

R2 and R3 are each independently a lower alkyl optionally comprising a terminal sulfonate group; and
R4 is H, OH or COOH.

\* \* \* \* \*